US007595297B2

(12) United States Patent
Tymianski

(10) Patent No.: US 7,595,297 B2
(45) Date of Patent: Sep. 29, 2009

(54) METHOD OF REDUCING INJURY TO MAMMALIAN CELLS

(76) Inventor: Michael Tymianski, 175 Dawlish Avenue, Toronto, Ontario (CA) M4N 1H6

( * ) Notice: Subject to any disclaimer, the term of this patent is extended or adjusted under 35 U.S.C. 154(b) by 329 days.

(21) Appl. No.: 10/208,374

(22) Filed: Jul. 30, 2002

(65) Prior Publication Data

US 2003/0050243 A1  Mar. 13, 2003

Related U.S. Application Data

(63) Continuation-in-part of application No. 09/584,555, filed on May 31, 2000, now abandoned.

(30) Foreign Application Priority Data

Jun. 2, 1999 (CA) ..................... 2273622

(51) Int. Cl.
*A61K 38/10* (2006.01)
*A61K 38/08* (2006.01)
*C07K 7/06* (2006.01)
*C07K 7/08* (2006.01)

(52) U.S. Cl. .............. 514/13; 530/326; 530/328; 514/15

(58) Field of Classification Search ............... None
See application file for complete search history.

(56) References Cited

U.S. PATENT DOCUMENTS

| 6,911,526 | B2 | 6/2005 | Sato et al. |
|---|---|---|---|
| 6,942,981 | B1 | 9/2005 | Lu et al. |
| 7,432,065 | B2 | 10/2008 | Lu et al. |
| 7,510,824 | B2 | 3/2009 | Tymianski |
| 7,514,224 | B2 | 4/2009 | Lu et al. |
| 2002/0147306 | A1* | 10/2002 | Lin et al. ............... 530/350 |
| 2005/0037969 | A1 | 2/2005 | Lu et al. |
| 2005/0059597 | A1 | 3/2005 | Tymianski |
| 2008/0274977 | A1 | 11/2008 | Belmares et al. |
| 2009/0062213 | A1 | 3/2009 | Belmares et al. |

FOREIGN PATENT DOCUMENTS

| CA | 2273622 A1 | | 2/2000 |
|---|---|---|---|
| WO | WO 97/33173 | * | 9/1997 |
| WO | WO 00/69896 | | 11/2000 |
| WO | WO 02/07751 A1 | | 1/2002 |

OTHER PUBLICATIONS

Fang et al. (2003) Journal of biological chemistry. 278, 38, 36669-36675.*
Saito et al (1997). Journal of Cerebral Blood Flow & Metabnolism. 17, 857-864 (herein numbered as pp. 1-12).*
Jaffery et al. (1998). Neuon. 20, 115-124.*
Hirbec et al. (2003). JBC. 277, 15221-15224.*
Schwarze et al.(1999) Science.285, 1569-1572.*
Cregan et al. (1997). J. Pharm. Exp. Therap. 283, 1412-1424.*
Hudzik et al. (1995). Epilepsy Res. 21, 183-193.*
Tatlisumak et al. (1998). Stroke. 29, 190-195.*
Cui 2007 (Journal of Neuroscience 27:9901-9915).*
Davis et al., "Selfotel in Acute Ischemic Stroke Possible Neurotoxic Effects of an NMDA Antagonist," *Stroke*, 31:347-354 (2000).
Fix et al., "Neuronal Vacuolization and Necrosis Induced by the Noncompetitive N-methyl-D-asparate (NMDA) Antagonist MK(+)801 (Dizocilpine Maleate): A Light and Electron Microscope Evaluation of the Rat Retrospinal Cortex," *Experimental Neurology*, 123:204-215 (1993).
Morris et al., "Failure of the competitive N-methyl-D-aspartate antagonist Selfotel (CGS 19755) in the treatment of severe head injury: results of two Phase III clinical trials,". *J. Neurosurg.*, 91:737-743 (1999).
Kornau et al., Science 269: 1737-1740, 1995.
Niethammer et al., Neuron 20: 693-707, 1998.
Wang et al., PNAS 93: 1721-1725, 1996.
Aarts et al., "Treatment of ischemic damage by perturbing NMDA receptor-PSD-95 protein interactions" *Science* 298, 846-850 (2002).
Beal, "Mechanisms of excitoxicity in neurologic diseases" *FASEB J.* 6, 3338-3344 (1992).
Meldrun et al., "Excitotoxicity and epileptic brain damage" *Epilepsy Res.10*, 55-61 (1991).
Tsai et al., "The glutamatergic basic of human alcoholism" *Am. J. Psychiatry 152*(3) 332-340 (1995).
Yamamoto et al., "Inhibition of nitric oxide synthesis increases focal ischemic infarction in rat" *J. Cereb. Blood Flow. Metab. 12*, 717-726 (1992).

(Continued)

*Primary Examiner*—Daniel E. Kolker
(74) *Attorney, Agent, or Firm*—Townsend and Townsend and Crew LLP; Joe Liebeschuetz

(57) ABSTRACT

A method of inhibiting the binding between N-methyl-D-aspartate receptors and neuronal proteins in a neuron the method comprising administering to the neuron an effective inhibiting amount of a peptide replacement agent for the NMDA receptor or neuronal protein interaction domain that effect said inhibition of the NMDA receptor neuronal protein. The method is of value in reducing the damaging effect of injury to mammalian cells. Postsynaptic density-95 protein (PSD-95) couples neuronal N-methyl-D-aspartate receptors (NMDARs) to pathways mediating excitotoxicity and ischemic brain damage. This coupling was disrupted by transducing neurons with peptides that bind to modular domains on either side of the PSD-95/NMDAR interaction complex. This treatment attenuated downstream NMDAR signaling without blocking NMDAR activity, protected cultured cortical neurons from excitotoxic insults and dramatically reduced cerebral infarction volume in rats subjected to transient focal cerebral ischemia. The treatment was effective when applied either before, or one hour after, the onset of excitotoxicity in vitro and cerebral ischemia in vivo. This approach prevents negative consequences associated with blocking NMDAR activity and constitutes practical therapy for stroke.

15 Claims, 8 Drawing Sheets

OTHER PUBLICATIONS

Buchan et al., "Failure to prevent selected CA1 neuronal death and reduce cortical infarction following cerebral ischemia with inhibition of nitric oxide synthase" *Neuroscience 61*(1), 1-11 (1994).

Dawson et al., "Inhibition of nitric oxide synthesis does not reduce infarct volume in a rat model of focal cerebral ischaemia" *Neurosci. Lett. 142*, 151-154 (1992).

Oransky, "NMDA receptors and stroke therapy" *The Lancet Neurology 1*, 463 (2002).

Jones, "Blocking the pathway to excitotoxicity" *Nature Reviews Neuroscience 3*, (2002).

Excerpt entitled: "New stroke drug may limit brain damage" *Canadian Press* (Oct. 25, 2002).

Excerpt entitled: "New drug prevents brain damage from stroke" Discoveryhealth.com (Oct. 25, 2002).

Porter, "Drug could ease strokes" thestar.com (Oct. 25, 2002).

McCook, "Researches prevent cell death in rats with stroke"Reuters.com, (Oct. 24, 2002).

Branswell, "New stroke drug shows promise in animal trials" *CTV.ca*, Canadian Press (ca. Oct. 25, 2002).

Smith, "Stroke drug could brain damage" *United Press International* (Oct. 24, 2002).

Excerpt entitled: "Strokes solutions" *CBC Radio One* (Oct. 25, 2002).

Porter, "Drug could ease strokes" *The Toronto Star* (Oct. 25, 2002).

Excerpt entitled "A gentler treatment for stroke" *Science 298*, 701 (Oct. 25, 2002).

Dyker et al., "Safety and tolerability study of Aptiganel Hydrochloride in patients with an acute ischemic stroke" *Stroke 30*, 2038-2042 (1999).

Lees, "Cerestat and other NMDA antagonists in ischemic stroke" *Neurology 49* (Supp. 4), S66-S69 (1997).

Muir et al., "Pharmacological effects of the non-competitive NMDA antagonist CNS 1102 in normal volunteers" *Br. J. clin. Pharmac. 38*, 33-38 (1994).

Grotta et al., "Safety and tolerability of the Glutamate antagonist CGS 19755 (Selfotel) in patients with acute ischemic stroke" *Stroke 26*, 602-605 (1995).

Davis et al., "Termination of acute stroke studies involving Selfotel treatment" *The Lancet 349*, 32 (1997).

Dotinga, "Synthetic protein protects rats from stroke" HealthCentral (Oct. 24, 2002).

Excerpt entitled: "Researchers prevent cell death in rats with stroke" *HeartCenterOnline for Patients*™ (Oct. 25, 2002).

Bassand et al.,"Differential interaction of the tSXV motifs of the NR1 and NR2A NMDA receptor subunits with PSD-95 and SAP97," *Eur. J. Neuroscience*, 11:2031-2043 (1999).

Bezprozvanny et al., "Classification of PDZ domains," *FEBS Letters*, 509:457-462 (2001).

Brenman et al., "Cloning and Characterization of Postsynaptic Density 93, a Nitric Oxide Synthase Interacting Protein," *J. Neuroscience*, 16(23):7407-7415 (1996).

Christopherson et al., "PSD-95 Assembles a Ternary Complex with N-Methyl-D-aspartic Acid Receptor and a Bivalent Neuronal NO Synthase PDZ Domain," *J. Biol. Chem.*, 274(39):27467-27473 (1999).

Cohen et al., "Binding of the inward rectifier K+ channel Kir 2.3 to PSD-95 is regulated by protein kinase A phosphorylation," *Neuron*, 17(4):759-767 (1996).

Doyle et al., "Crystal structures of a complexed and peptide-free membrane protein-binding domain: molecular basis of peptide recognition by PDZ," *Cell*, 85(7):1067-1076 (1996).

El-Maghrabi et al., "Saturable binding of halothane to rat brain synaptosomes," *PNAS*, 89:4329-4332 (1992).

Ferrer-Montiel et al., "Selected peptides targeted to the NMDA receptor channel protect neurons from excitotoxic death," *Nature Biotechnology*, 16(3):286-291 (1998).

Fuh et al., "Analysis of PDZ Domain-Ligand Interactions Using Carboxyl-terminal Phage Display," *J. Biol. Chem.*, 275(28):21486-21491 (2000).

Gee et al., "Single-amino acid substitutions alter the specificity and affinity of PDZ domains for their ligands," *Biochemistry*, 39(47):14638-14646 (2000).

Harris et al., "Mechanism and role of PDZ domains in signaling complex assembly," *J. Cell Science*, 114:3219-3231 (2001).

Horio et al., "Clustering and Enhanced Activity of an Inwardly Rectifying Potassium Channel, Kir4.1, by an Anchoring Protein, PSD-95/SAP90," *J. Biol. Chem.*, 272(20):12885-12888 (1997).

Hsueh et al., "Disulfide-Linked Head-to-Head Multimerization in the Mechanism of Ion Channel Clustering by PSD-95," *Neuron*, 18:803-814 (1997).

Hu et al., "$\beta_1$-Adrenergic Receptor Association with PSD-95," *J. Biol. Chem.*, 275(49):38659-38666 (2000).

Im et al., "Crystal Structure of the Shank PDZ-Ligand Complex Reveals a Class 1 PDZ Interaction and a Novel PDZ-PDZ Dimerization," *J. Biol. Chem.*, 278(48):48099-48104 (2003).

Irie et al., "Binding of Neuroligins to PSD-95," *Science*, 277:1511-1515 (1997).

Kim et al., "Plasma Membrane $Ca^{2+}$ATPase Isoform 4b Binds to Membrane-associated Guanylate Kinase (MAGUK) Proteins via Their PDZ (PSD-95/D1g/ZO-1) Domains," *J. Biol. Chem.*, 273(3):1591-1595 (1998).

Kim et al., "Clustering of Shaker-type K+ channels by interaction with a family of membrane-associated guanylate kinases " *Nature*, 378(6652):85-88 (1995).

Lim et al., "Selectivity and Promiscuity of the First and Second PDZ Domains of PSD-95 and Synapse-assoicated Protein 102," *J. Biol. Chem.*, 277(24):21697-21711 (2002).

Matsumine et al., "Binding of APC to the human homolog of the *Drosophila* discs large tumor suppressor protein," *Science*, 272(5264):974-975 (1996).

Muler et al., "Molecular Characterization and Spatial Distribution of SAP97, a Novel Presynaptic Protein Homologous to SAP90 and the *Drosophilia* Discs-Large Tumor Suppressor Protein," *J. Neuroscience*, 15(3):2354-2366 (1995).

Niethammer et al., "Interaction between the C Terminus of NMDA Receptor Subunits and Multiple Members of the PSD-95 Family of Membrane-Associated Guanylate Kinases," *J. Neuroscience*, 16(7):2157-2163 (1996).

O'Brien et al., "Molecular mechanisms of glutamate receptor clustering at excitatory synapses," *Curr. Opin. Neurobiol.*, 8(3):364-369 (1998).

Saro et al., "Thermodynamic analysis of a hydrophobic binding site: probing the PDZ domain with nonproteinogenic peptide ligands," *Org. Lett.*, 6(20):3429-3432 (2004).

Shan al., "Identification of a specific inhibitor of the disheveled PDZ domain," *Biochemistry*, 44(47):15495-15503 (2005).

Sheng et al., "PDZ domains and the organization of supramolecular complexes," *Annu. Rev. Neurosci.*, 24:1-29 (2001).

Songyang et al., "Recognition of Unique Carboxyl-Terminal Motifs by Distinct PDZ Domains," *Science*, 275:73-77 (1997).

Thomas et al., "Synaptic clustering of the cell adhesion molecule fasciclin II by discs-large and its role in the regulation of presynaptic structure," *Neuron*, 19(4):787-799 (1997).

Wang et al., "Formation of a native-like beta-haripin finger structure of a peptide from the extended PDZ domain of neuronal nitric oxide synthase in aqueous solution," *Eur. J. Biochem.*, 267(11):3116-3122 (2000).

Yanagisawa et al., "The Molecular Interaction of Fas and Fap-1, A Tripeptide Blocker of Human Fas Interaction with FAP-1 Promotes Fas-Induced Apoptosis,", *J. Biol. Chem.*, 272(13):8539-8545 (1997).

U.S. Appl. No. 11/894,818, filed Aug. 20, 2007, Tymianski.

U.S. Appl. No. 12/392,988, filed Feb. 25, 2009, Tymianski.

Arundine, et al., "Glutamatergic Mechaisms of Isolated Secondary Traumatic Neuronal Injury in Vitro", *Society for Neuroscience Abstracts*, 27(1):569, (2001). abstract only.

Brenman, et al., "Cloning and Characterization of Postsynaptic Density 93, a Nitric Oxide Synthase Interacting Protein", *J. of Neuroscience*, 16(23):7407-7415, (1996).

Cheng et al., "Structure-based maximal affinity model predicts small-molecule druggability", *Nature Biotech.*, 25(1):71-75, (2007).

Frankel et al., "Cellular Uptake of the Tat Protein from Human Immunodeficiency Virus", *Cell*, 55:1189-1193, (1988).

Hayman et al., "Neurotoxicity of Peptide Analogues of the Transactivating Protein tat from Maedi-Visna Virus and Human Immunodeficiency Virus", *Neuroscience*, 53(1):1-6, (1993).

Liu, "Uncoupling NMDA Receptor—PSD—95 Protein Interactions Reduces Infarction in Focal Cerebral Ischemia in Rats", *Society for Neuroscience Abstract Viewer and Itinerary Planner*, 2002:245.3, (2002). abstract only.

Macarron, "Critical review of the role of HTS in drug discovery", *Drug Discovery Today*, 11(7/8):277-279, (2006).

Sabatier et al., "Evidence for Neurotoxic Activity of *tat* from Human Immunodeficiency Virus Type 1", *J. of Virology*, 65(2):961-967, (1991).

Sattler, et al., "Specific Coupling of NMDA Receptor Activation to Nitric Oxide Neurotoxicity by PSD-95 Protein", *Science*, 284(5421):1845-8, (1999).

Vivès et al., "A Truncated HIV-1 Tat Protein Basic Domain Rapidly Translocates through the Plasma Membrane and Accumulates in the Cell Nucleus", *J. Biological Chemistry*, 272(25):16010-16017, (1997).

Weeks et al., "Neurotoxicity of the Human Immunodeficiency Virus Type 1 Tat Transactivator to PC12 Cells Requires the Tat Amino Acid 49-58 Basic Domain", *J of Neuroscience Research*, 42:34-40, (1995).

U.S. Appl. No. 10/938,249, Office Action mailed Oct. 30, 2007.
U.S. Appl. No. 10/938,249, Final Office Action mailed Jun. 23, 2008.
U.S. Appl. No. 10/938,249, Final Office Action mailed Jan. 02, 2009.
Arundine et al (2003). J Neurotrauma. 20,1377-1396.

Liu et al., "Uncoupling NMDA Receptor—PSD-95 Protein Interactions Reduces Infarction in Focal Cerebral Ischemia in Rats", Soc. Neurosci. Abstract Viewer and Itinerary Planner, vol. 2002, 2002, p. Abstract No. 245.3. from $32^{nd}$ Annual Meeting of the Society of Neuroscience, Orlando Florida, Nov. 2-7, 2002.

U.S. Appl. No. 09/584,555, Office Action mailed Jun. 10, 2002.
U.S. Appl. No. 10/930,192, Office Action mailed Oct. 03, 2007.
U.S. Appl. No. 10/930,192, Final Office Action mailed Apr. 29, 2008.
U.S. Appl. No. 10/930,192, Notice of Allowance mailed Nov. 18, 2008.

\* cited by examiner

METHOD OF REDUCING INJURY TO MAMMALIAN CELLS

RELATED APPLICATION

This application is a continuation-in-part application of Ser. No. 09/584,555, filed May 31, 2000.

FIELD OF THE INVENTION

This invention relates to methods of reducing the damaging effect of an injury to mammalian cells by treatment with compounds which reduce the binding between N-methyl-D-aspartate receptors and neuronal proteins; pharmaceutical compositions comprising said compounds and methods for the preparation of said pharmaceutical compositions.

BACKGROUND TO THE INVENTION

Ischemic or traumatic injuries to the brain or spinal cord often produce irreversible damage to central nervous system (CNS) neurons and to their processes. These injuries are major problems to society as they occur frequently, the damage is often severe, and at present there are still no effective pharmacological treatments for acute CNS injuries. Clinically, ischemic cerebral stroke or spinal cord injuries manifest themselves as acute deteriorations in neurological capacity ranging from small focal defects, to catastrophic global dysfunction, to death. It is currently felt that the final magnitude of the deficit is dictated by the nature and extent of the primary physical insult, and by a time-dependent sequence of evolving secondary phenomena which cause further neuronal death. Thus, there exists a theoretical time-window, of uncertain duration, in which a timely intervention might interrupt the events causing delayed neurotoxicity. However, little is known about the cellular mechanisms triggering and maintaining the processes of ischemic or traumatic neuronal death, making it difficult to devise practical preventative strategies. Consequently, there are currently no clinically useful pharmacological treatments for cerebral stroke or spinal cord injury.

In vivo, a local reduction in CNS tissue perfusion mediates neuronal death in both hypoxic and traumatic CNS injuries. Local hypoperfusion is usually caused by a physical disruption of the local vasculature, vessel thrombosis, vasospasm, or luminal occlusion by an embolic mass. Regardless of its etiology, the resulting ischemia is believed to damage susceptible neurons by impacting adversely on a variety of cellular homeostatic mechanisms. Although the nature of the exact disturbances is poorly understood, a feature common to many experimental models of neuronal injury is a rise in free intracellular calcium concentration ($[Ca^{2+}]i$). Neurons possess multiple mechanisms to confine $[Ca^{2+}]_i$ to the low levels, about 100 nM necessary for the physiological function. It is widely believed that a prolonged rise in $[Ca^{2+}]_i$ deregulates tightly-controlled $Ca^{2+}$-dependent processes, causing them to yield excessive reaction products, to activate normally quiescent enzymatic pathways, or to inactivate regulatory cytoprotective mechanisms. This, in-turn, results in the creation of experimentally observable measures of cell destruction, such as lipolysis, proteolysis, cytoskeletal breakdown, pH alterations and free radical formation.

The classical approach to preventing $Ca^{2+}$ neurotoxicity has been through pharmacological blockade of $Ca^{2+}$ entry through $Ca^{2+}$ channels and/or of excitatory amino acid (EAA)—gated channels. Variations on this strategy often lessen EAA-induced or anoxic cell death in vitro, lending credence to the $Ca^{2+}$-neurotoxicity hypothesis. However, a variety of $Ca^{2+}$ channel- and EAA-antagonists fail to protect against neuronal injury in vivo, particularly in experimental Spinal Cord Injury (SCI), head injury and global cerebral ischemia. It is unknown whether this is due to insufficient drug concentrations, inappropriate $Ca^{2+}$ influx blockade, or to a contribution from non-$Ca^{2+}$ dependent neurotoxic processes. It is likely that $Ca^{2+}$ neurotoxicity is triggered through different pathways in different CNS neuron types. Hence, successful $Ca^{2+}$-blockade would require a polypharmaceutical approach.

As a result of investigations, I have discovered methods of reducing the damaging effect of an injury to mammalian cells by treatment with compounds to reduce the binding between N-methyl-D-aspartate (NMDA) receptors and neuronal proteins.

PUBLICATIONS

1. A. Ghosh, M. E. Greenberg, *Science* 268, 239 (1995); T. V. Bliss, G. L. Collingridge, *Nature* 361, 31 (1993).
2. J. W. Olney, *Kainic acid as a tool in neurobiology*., E. G. McGeer, J. W. Olney and P. L. McGeer, Eds. (Raven Press, New York, 1978), p. 95.; S. M. Rothman, J. W. Olney, *TINS* 10, 299 (1987).; D. W. Choi, *Ann NY Acad Sci* 747, 162 (1994).
3. S. A. Lipton, P. A. Rosenberg, *New Eng J Med* 330, 613 (1994).
4. R. Sattler, M. P. Charlton, M. Hafner, M. Tymianski, *J Neurochem* 71, 2349 (1998).; M. Tymianski, M. P. Charlton, P. L. Carlen, C. H. Tator, *J Neurosci* 13, 2085 (1993).
5. K. O. Cho, C. A. Hunt, M. B. Kennedy, *Neuron* 9, 929 (1992).
6. H. C. Kornau, L. T. Schenker, M. B. Kennedy, P. H. Seeburg, *Science* 269, 1737 (1995).; J. E. Brenman, K. S. Christopherson, S. E. Craven, A. W. McGee, D. S. Bredt, *J Neurosci* 16, 7407 (1996).; B. M. Muller, et al, *Neuron* 17, 255 (1996).
7. H. Dong, et al, *Nature* 386, 279 (1997).; P. R. Brakeman, et al, *Nature* 386, 284 (1997).
8. S. E. Craven, D. S. Bredt, *Cell* 93, 495 (1998).; M. Niethammer, et al, *Neuron* 20, 693 (1998).; J. H. Kim, D. Liao, L. F. Lau, R. L. Huganir, *Neuron* 20, 683 (1998).; T. Tezuka, H. Umemori, T. Akiyama, Nakanishi, T. Yamamoto, *Proc Natl Acad Sci USA* 96, 435(1999).
9. Hertz, E., Yu, A. C. H., Hertz, L., Juurlink, B. H. J. & Schousboe, A. in *A dissection and tissue culture manual of the nervous system* (eds Shahar, A., de Vellis, J., Vernadakis, A. & Haber, B.) Vol.1, 183-186 (Alan R. Liss Inc., New York, 1989).
10. S. F. Altschul, et al, *Nucleic Acids Research* 25, 3389 (1997).
11. O. T. Jones, et al, *J Neurosci* 17, 6152 (1997).
12. V. L. Dawson, T. M. Dawson, E. D. London, D. S. Bredt, S. H. Snyder, *Proc Natl Acad Sci USA* 88, 6368 (1991).; V. L. Dawson, T. M. Dawson, D. A. Bartley, G. R. Uhl, S. H. Snyder, *J Neurosci* 13, 2651 (1993).; T. M. Dawson, D. S. Bredt, M. Fotuhi, P. M. Hwang, S. H. Snyder, *Proc Natl Acad Sci USA* 88, 7797 (1991).
13. Xiong, Z., Lu, W. & MacDonald, J. F. *proc Natl Acad Sci USA* 94, 7012-7017 (1997).
14. R. Sattler, M. P. Charlton, M. Hafner, M. Tymianski, *J Cereb Blood Flow Metab* 17, 455 (1997).
15. N. Burnashev, Z. Zhou, E. Neher, B. Sakmann, *J Physiol* 485, 403 (1995).
16. M. Migaud, et al, *Nature* 396, 433 (1998).

17. J. R. Brorson, P. T. Schumacker, H. Zhang, *J Neurosci* 19, 147 (1999).
18. S. R. Jaffrey, S. H. Snyder, *Annual Review of Cell & Developmental Biology* 11, 417 (1995).
19. S. R. Jaffrey, S. H. Snyder, *Annual Review of Cell & Developmental Biology* 11, 417 (1995).
20. T. Pawson and J. D. Scott, *Science* 278, 2075-2080 (1997).
21. M. Sheng, *Proc. Natl. Acad. Sci. U.S.A* 98, 7058-7061 (2001).
22. J. E. Brenman et al., *Cell* 84, 757-767 (1996).
23. V. L. Dawson, T. M. Dawson, E. D. London, D. S. Bredt, S. H. Snyder, *Proc Natl Acad Sci USA* 88, 6368-6371 (1991).
24. M. Migaud et al., *Nature* 396, 433-439 (1998).
25. R. Sattler et al., *Science* 284, 1845-1848 (1999).
26. R. P. Simon, J. H. Swan, B. S. Meldrum, *Science* 226, 850-852 (1984).
27. A. S. Fix et al., *Exp Neurol* 123, 204-215 (1993).
28. S. M. Davis et al., *Stroke* 31, 347-354 (2000).
29. G. F. Morris et al., *J. Neurosurg.* 91, 737-743 (1999).
30. S. R. Schwarze, A. Ho, A. Vocero-Akbani, S. F. Dowdy, *Science* 285, 1569-1572 (1999).
31. D. A. Mann and A. D. Frankel, *EMBO J.* 10, 1733-1739 (1991).
32. R. Sattler, M. P. Charlton, M. Hafner, M. Tymianski, *J Neurochem* 71, 2349-2364 (1998).
33. R. Sattler, Z. Xiong, W. Y. Lu, J. F. McDonald, M. Tymianski, *J. Neurosci.* 20, 22-33 (2000).
34. S. R. Jaffrey and S. H. Snyder, *Annual Review of Cell & Developmental Biology* 11, 417-440 (1995).
35. U. Kistner, C. C. Garner, M. Linial, *FEBS Lett.* 359, 159-163 (1995).
36. E. Z. Longa, P. R. Weinstein, S. Carlson, R. Cummins, *Stroke* 20, 84-91 (1989).
37. L. Belayev, O. F. Alonso, R. Busto, W. Zhao, M. D. Ginsberg, *Stroke* 27, 1616-1622 (1996).
38. J. B. Bederson et al., *Stroke* 17, 472-476 (1986).
39. M. De Ryck, J. van Reempts, M. Borgers, A. Wauquier, P. A. Janssen, *Stroke* 20, 1383-1390 (1989).

SUMMARY OF THE INVENTION

I have found that postsynaptic density-95 protein (PSD-95) couples neuronal N-methyl-D-aspartate receptors (NMDARs) to pathways mediating excitotoxicity and ischemic brain damage. This coupling was disrupted by transducing neurons with peptides that bind to modular domains on either side of the PSD-95/NMDAR interaction complex. This treatment attenuated downstream NMDAR signaling without blocking NMDAR activity, protected cultured cortical neurons from excitotoxic insults and dramatically reduced cerebral infarction volume in rats subjected to transient focal cerebral ischemia. The treatment was effective when applied either before, or one hour after, the onset of excitotoxicity in vitro and cerebral ischemia in vivo. This approach may prevent negative consequences associated with blocking NMDAR activity and constitute a practical therapy for stroke.

It is an object of the present invention to provide in its broadest aspect a method of reducing the damaging effect of an injury to mammalian cells.

In a preferred object, the invention provides pharmaceutical compositions for use in treating mammals to reduce the damaging effect of an injury to mammalian tissue.

The present invention is based on the discovery of a neuroprotective effect against excitotoxic and ischemic injury by inhibiting the binding between N-methyl-D-aspartate (NMDA) receptors and neuronal proteins in a neuron.

Accordingly, in one aspect the invention provides a method of inhibiting the binding between N-methyl-D-aspartate receptors and neuronal proteins in a neuron said method comprising administering to said neuron an effective inhibiting amount of a peptide replacement agent for the NMDA receptor interaction domain to effect said inhibition of the interaction with the neuronal protein.

In a further aspect, the invention provides a method of inhibiting the binding between N-methyl-D-aspartate receptors and neuronal proteins in a neuron said method comprising administering to said neuron an effective inhibiting amount of a peptide replacement agent for the neuronal protein interaction domain to effect said inhibition of the interaction with the NMDA receptor.

In a further aspect, the invention provides a method of reducing the damaging effect of ischemia or traumatic injury to the brain or spinal cord in a mammal, said method comprising treating said mammal with a non-toxic, damage-reducing, effective amount of a peptide replacement agent for the NMDA receptor or neuronal protein interaction domains that inhibit the NMDA receptor neuronal protein interaction.

Damage to neurons in this specification is meant anoxia, ischemia, excitotoxicity, lack of neurotrophic support, disconnection, and mechanical injury.

The NMDA agent is, preferably, bindable with proteins containing PDZ domains, and most preferably, is selected from postsynaptic density-95 proteins, PSD-95, PSD-93 and SAP102.

I have found that the replacement agent is a tSXV-containing peptide, wherein the motif tSXV represents both TXV-containing peptides and SXV-containing peptides, preferably KLSSIESDV (SEQ. ID NO: 1) or KLSSIETDV (SEQ ID NO: 6).

The neuronal protein agent is, preferably, bindable with excitatory amino acid receptors, and most preferably, is selected from NMDA receptor subunits NR1 and NR2.

I have found that the replacement agent is a PDZ2-domain containing polypeptide, preferably corresponding to residues 65-248 of PSD-95, encoding the first and second PDZ domains (PDZ1-2) of PSD-95.

In a yet further aspect the invention provides a pharmaceutical composition comprising a peptide replacement agent for the NMDA receptor or neuronal protein interaction domains that inhibit the NMDA receptor neuronal protein interaction in a mixture with a pharmaceutically acceptable carrier when used for reducing the damaging effect of an ischemic or traumatic injury to the brain or spinal chord of a mammal; preferably further comprising the cell-membrane transduction domain of the human immunodeficiency virus type 1 (HIV-1) Tat protein (YGRKKRRQRRR (SEQ ID No: 2); Tat), or the antennapedia internalisation peptide.

In a most preferred aspect, the invention provides a pharmaceutical composition comprising the peptide KLSSIESDV (SEQ ID NO: 1) or residues 65-248 of PSD-95, encoding the first and second PDZ domains (PDZ1-2) of PSD-95.

In a further aspect, the invention provides a method of inhibiting the binding between NMDA receptors and neuronal proteins in a neuron, said method comprising administering to said neuron an effective inhibiting amount of an antisense DNA to prevent expression of said neuronal proteins to effect inhibition of said binding. Preferably, this aspect provides a method wherein said antisense DNA reduces the expression of a protein containing PDZ domains bindable to said NMDA receptor. More preferably, the protein containing PDZ domains is selected from PSD-95, PSD-93 and SAP102.

In the mammalian nervous system, the efficiency by which N-methyl-D-aspartate receptor (NMDAR) activity triggers intracellular signaling pathways governs neuronal plasticity, development, senescence and disease. I have studied excitotoxic NMDAR signaling by suppressing the expression of the NMDAR scaffolding protein PSD-95. In cultured cortical neurons, this selectively attenuated NMDAR excitotoxicity, but not excitotoxicity by other glutamate or $Ca^{2+}$ channels. NMDAR function was unaffected, as receptor expression, while NMDA-currents and $^{45}Ca$ loading via NMDARs were unchanged. Suppressing PSD-95 selectively blocked $Ca^{2+}$-activated nitric oxide production by NMDARs, but not by other pathways, without affecting neuronal nitric oxide synthase (nNOS) expression or function. Thus, PSD-95 is required for the efficient coupling of NMDAR activity to nitric oxide toxicity and imparts specificity to excitotoxic $Ca^{2+}$ signaling.

It is known that calcium influx through NMDARs plays key roles in mediating synaptic transmission, neuronal development, and plasticity (1). In excess, Ca influx triggers excitotoxicity (2), a process that damages neurons in neurological disorders that include stroke, epilepsy, and chronic neurodegenerative conditions (3). Rapid $Ca^{2+}$-dependent neurotoxicity is triggered most efficiently when $Ca^{2+}$ influx occurs through NMDARs, and cannot be reproduced by loading neurons with equivalent quantities of $Ca^{2+}$ through non-NMDARs or voltage-sensitive $Ca^{2+}$ channels (VSCCs) (4). This observation suggests that $Ca^{2+}$ influx through NMDAR channels is functionally coupled to neurotoxic signaling pathways.

Without being bound by theory, I believe that lethal $Ca^{2+}$ signaling by NMDARs is determined by the molecules with which they physically interact. The NR2 NMDAR subunits, through their intracellular C-terminal domains, bind to PSD-95/SAP90 (5), chapsyn-110/PSD-93, and other members of the membrane-associated guanylate kinase (MAGUK) family (6). NMDAR-bound MAGUKs are generally distinct from those associated with non-NMDARs (7). I have found that the preferential activation of neurotoxic $Ca^{2+}$ signals by NMDARs is determined by the distinctiveness of NMDAR-bound MAGUKs, or of the intracellular proteins that they bind. PSD-95 is a submembrane scaffolding molecule that binds and clusters NMDARs preferentially and, through additional protein-protein interactions, may link them to intracellular signaling molecules (8). Perturbing PSD-95 would impact on neurotoxic $Ca^{2+}$ signaling through NMDARs.

Thus, protein-protein interactions govern the signals involved in cell growth, differentiation, and intercellular communication through dynamic associations between modular protein domains and their cognate binding partners (20). At excitatory synapses of central neurons, ionotropic glutamate receptors are organized into multi-protein signaling complexes within the post-synaptic density (PSD) (21). A prominent organizing protein within the PSD is PSD-95, a member of the membrane-associated guanylate kinase (MAGUK) family. PSD-95 contains multiple domains that couple transmembrane proteins such as the N-methyl-D-aspartate subtype of glutamate receptors (NMDAR) to a variety of intracellular signaling enzymes (21,22). Through its second PDZ domain (PDZ2), PSD-95 binds both the NMDAR 2B subunit (NR2B) and neuronal nitric oxide synthase (nNOS) (22). This interaction couples NMDAR activity to the production of nitric oxide (NO), a signaling molecule that mediates NMDAR-dependent excitotoxicity (23). Research has shown that NMDAR function is unaffected by genetically disrupting PSD-95 in vivo (24) or by suppressing its expression in vitro (25). Nonetheless, PSD-95 deletion dissociates NMDAR activity from NO production and suppresses NMDAR-dependent excitotoxicity.

Although NMDARs play an important neurotoxic role in hypoxic/ischemic brain injury (26), blocking NMDAR function may be deleterious in animals and humans (27-29). Targeting PSD-95 protein therefore represents an alternative therapeutic approach for diseases that involve excitotoxicity that may circumvent the negative consequences of blocking NMDAR function. However, mutation or suppression of PSD-95 is impractical as a therapy for brain injury and cannot be applied after an injury has occurred. Therefore, rather than alter PSD-95 expression, I questioned whether interfering with the NMDAR/PSD-95 interaction could suppress excitotoxicity in vitro and ischemic brain damage in vivo.

BRIEF DESCRIPTION OF THE DRAWINGS

In order that the invention may be better understood preferred embodiments will now be described by way of example only with reference to the accompanying drawings wherein:

FIG. 1a is an immunoblot;

FIG. 1b is a bar chart providing densitometric analysis of PSD-95 expression;

FIG. 1c represents representative phase contrast and propidium fluorescence images;

FIG. 1d is a bar chart of NMDA concentration against fraction of dead cells;

FIG. 1e is a bar chart of NMDA concentration against Calcium accumulation.

DETAILED DESCRIPTION OF PREFERRED EMBODIMENTS

Figure 1:
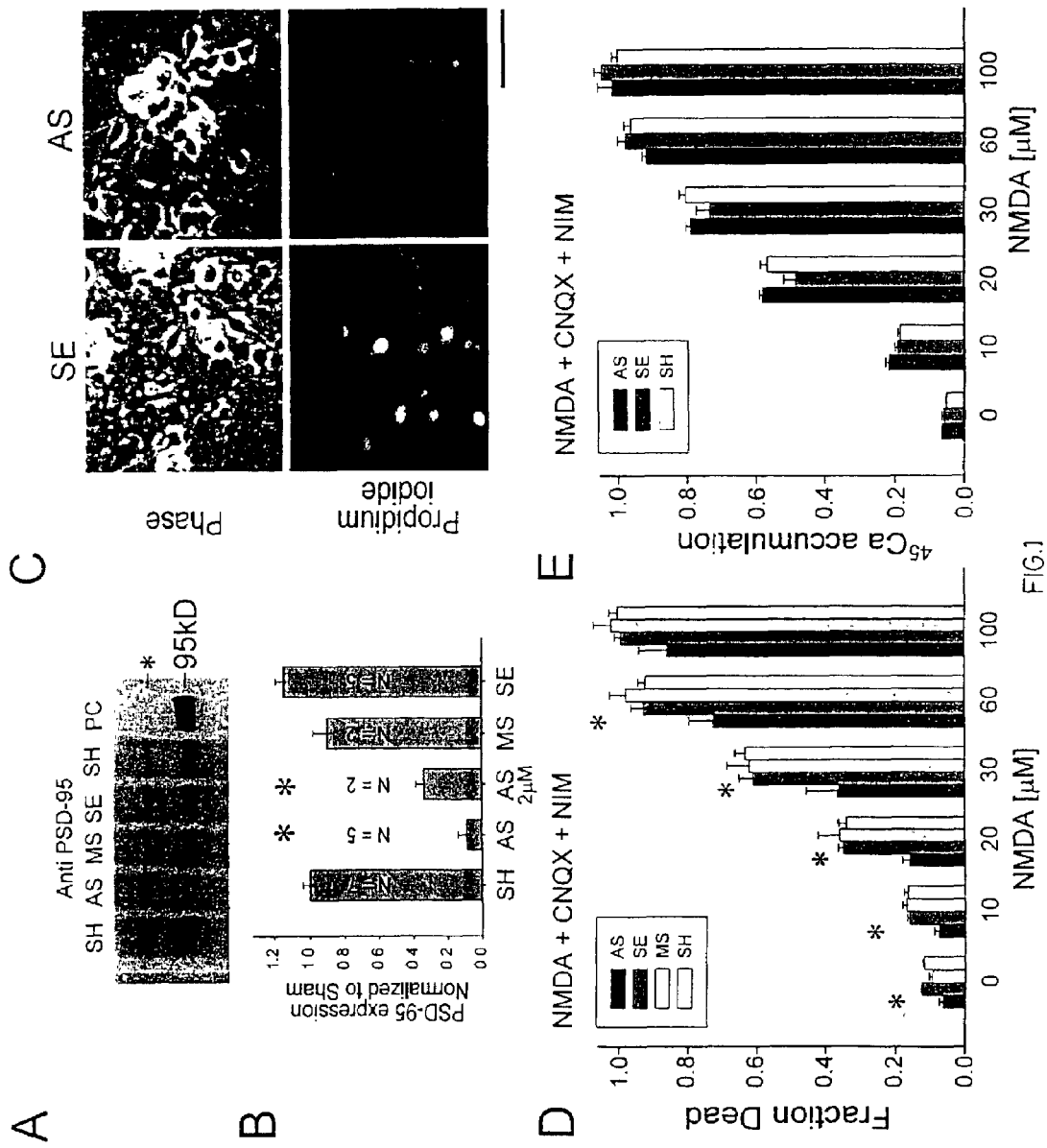
FIGS. 2a1-b2 represent bar charts of selective activations of AMPA/Kainate receptors with Kainate (2a1 and 2-a2); and loadings with Vscc's (2-b1) and calcium loading (2-b2).

Methods:

Cultured cortical neurons were prepared by standard techniques (4,9) and switched to serum-free media at 24 h [Neurobasal with B27 supplement (Gibco)]. The AS ODN corresponded to nucleotides 435-449 of mouse PSD-95/SAP90 mRNA (GeneBank Acc. No. D50621). Filter-sterilized phosphodiester AS SE, and MS ODNs (5 μM) were added in culture medium during feedings at 4,6,8 and 10 days after plating. Cultures were used for all experiments (FIGS. 1-4) on day 12. ODN sequences exhibited no similarity to any other known mammalian genes (BLAST search (10)).

Immunoblotting was done as described in ref. "26". Tissue was harvested and pooled from 2 cultures/lane. The blotted proteins were probed using a monoclonal anti-PSD-95 mouse IgG1 (Transduction Labs, 1:250 dilution), polyclonal anti PSD-93 (1:1000 dilution) and anti SAP-102 (1:2000 dilution) rabbit serum antibodies (Synaptic Systems GmbH), a monoclonal anti NR1 mouse IgG2a (PharMingen Canada, 1:1000 dilution) or a monoclonal anti nNOS (NOS type I) mouse IgG2a (Transduction Labs, 1:2500 dilution). Secondary antibodies were sheep anti-mouse, or donkey anti-rabbit Ig conjugated to horseradish peroxidase (Amersham). Immunoblots for PSD-95 were obtained for all experiments (FIGS. 1-4) from sister cultures, and all gels quantified using an imaging densitometer (Bio-Rad GS-670).

cGMP determinations were performed 10 min after challenging the cultures with NMDA, kainate, or high-K (FIGS. 4c-e) with the Biotrak cGMP enzymeimmunoassay system according to the kit manufacturer's instructions (Amersham). Staining for NADPH diaphorase (FIG. 4b) was done as described in ref. 12.

Electrophysiology. Whole cell patch-clamp recordings in the cultured neurons were performed and analyzed as described in ref. 13. During each experiment a voltage step of −10 mV was applied from holding potential and the cell capacitance was calculated by integrating the capacitative transient. The extracellular solution contained (in mM): 140 NaCl, 5.4 KCl, 1.3 $CaCl_2$, 25 HEPES, 33 glucose, 0.01 glycine, and 0.001 tetrodotoxin (pH=7.3-7.4, 320-335 mOsm). A multi-barrel perfusion system was employed to rapidly exchange NMDA containing solutions. The pipette solution contained (in mM): 140 CsF, 35 CsOH, 10 HEPES, 11 EGTA, 2 tetraethylammonium chloride (TEA), 1 $CaCl_2$, 4 MgATP, pH 7.3 at 300 mOsm. Lucifer yellow (LY; 0.5% w/v) was included in the pipette for experiments in FIG. 3d.

Excitotoxicity and $Ca^{2+}$ accumulation measurements were performed identically to the methods described and validated in refs. 4 and 14. We used measurements of propidium iodide fluorescence as an index of cell death, and of radiolabelled $^{45}Ca^{2+}$ accumulation for $Ca^{2+}$ load determinations in sister cultures on the same day. Experimental solutions were as previously described (4). $Ca^{2+}$ influx was pharmacologically channeled through distinct pathways as follows: To NMDARs by applying NMDA (×60 min) in the presence of both CNQX (Research Biochemicals Inc) and nimodipine (Miles Pharmaceuticals), to non-NMDARs by applying kainic acid (×60 min or 24 h) in the presence of both MK-801 (RBI) and nimodipine, and to VSCCs using 50 mM K+ solution (×60 min) containing 10 mM $Ca^{2+}$ and S(−)-Bay K 8644, an L-type channel agonist (300-500 nM; RBI), MK-801 and CNQX. Antagonist concentrations were (in μM): MK-801 10, CNQX 10, nimodipine 2. All three antagonists were added after the 60 min agonist applications for the remainder of all experiments (24 h). A validation of this approach in isolating $Ca^{2+}$ influx to the desired pathway in our cortical cultures has been published (4).

Whole cell patch-clamp recordings in the cultured neurons were performed and analyzed as described in Z. Xiong, W. Lu, J. F. MacDonald, *Proc Natl Acad Sci USA* 94, 7012 (1997). During each experiment a voltage step of −10 mV was applied from holding potential and the cell capacitance was calculated by integrating the capacitative transient. The extracellular solution contained (in mM): 140 NaCl, 5.4 KCl, 1.3 $CaCl_2$, 25 HEPES, 33 glucose, 0.01 glycine, and 0.001 tetrodotoxin (pH=7.3-7.4, 320-335 mOsm). A multi-barrel perfusion system was employed to rapidly exchange NMDA containing solutions. The pipette solution contained (in mM): 140 CsF, 35 CsOH, 10 HEPES, 11 EGTA, 2 tetraethylammonium chloride (TEA), 1 $CaCl_2$, 4 MgATP, pH 7.3 at 300 mOsm. Lucifer yellow (LY; 0.5% w/v) was included in the pipette for experiments in FIG. 3D.

Data analysis: data in all figures were analyzed by ANOVA, with a post-hoc Student's t-test using the Bonferroni correction for multiple comparisons. All means are presented with their standard errors.

In greater detail:

FIG. 1, shows increased resilience of PSD-95 deficient neurons to NMDA toxicity in spite of $Ca^{2+}$ loading. A. Immunoblot showing representative effects of sham (SH) washes, and PSD-95 AS, SE and MS ODNs, on PSD-95 expression. PC: positive control tissue from purified rat brain cell membranes. Asterisk: non-specific band produced by the secondary antibody, useful to control for protein loading and blot exposure times. B. Densitometric analysis of PSD-95 expression pooled from N experiments. Asterisk: different from other groups, one-way ANOVA, F=102, p<0.0001. ODNs were used at 5 μM except where indicated (AS 2 μM). C. Representative phase contrast and propidium iodide fluorescence images of PSD-95 deficient (AS) and control (SE) cultures 24 h after a 60 min challenge with 30 μM NMDA. Scale bar: 100 μm. D. Decreased NMDA toxicity at 24 h in PSD-95 deficient neurons following selective NMDAR activation×60 min (n=16 cultures/bar pooled from N=4 separate experiments). Asterisk: differences from SE, MS and SH (Bonferroni t-test, p<0.005). Death is expressed as the fraction of dead cells produced by 100 μM NMDA in sham-ODN-treated controls (validated in 4,14). E. No effect of PSD-95 deficiency on NMDAR-mediated $Ca^{2+}$ loading (n=12/bar, N=3; reported as the fraction of $^{45}Ca^{2+}$ accumulation achievable over 60 min in the sham controls by 100 μM NMDA, which maximally loads the cells with calcium (4).

Figure 2:
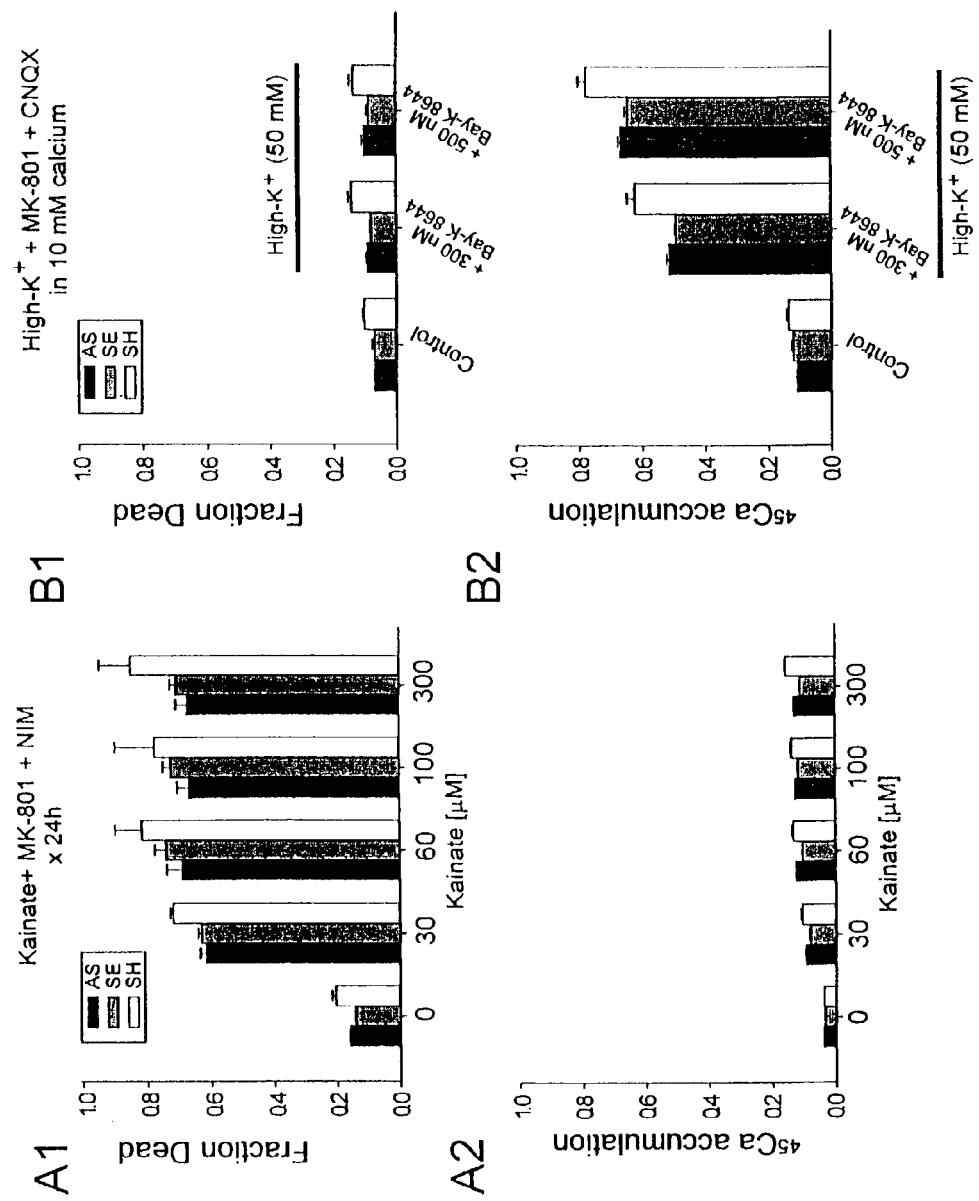

FIG. 2, shows that PSD-95 deficiency does not affect toxicity and $Ca^{2+}$ loading produced by activating non-NMDARs and $Ca^{2+}$ channels. Cultures were treated with SH washes or AS or SE ODNs as in FIG. 1. A. Selective activation of AMPA/kainate receptors with kainate in MK-801 (10 μM) and nimodipine (NIM; 2 μM) produces toxicity over 24 h (A1) irrespective of PSD-95 deficiency, with minimal $^{45}Ca^{2+}$ loading (A2). B. Selective activation of VSCCs produces little toxicity (B1), but significant $^{45}Ca^{2+}$ loading (B2) that is also insensitive to PSD-95 deficiency. n=4 cultures/bar in all experiments.

Figure 3:
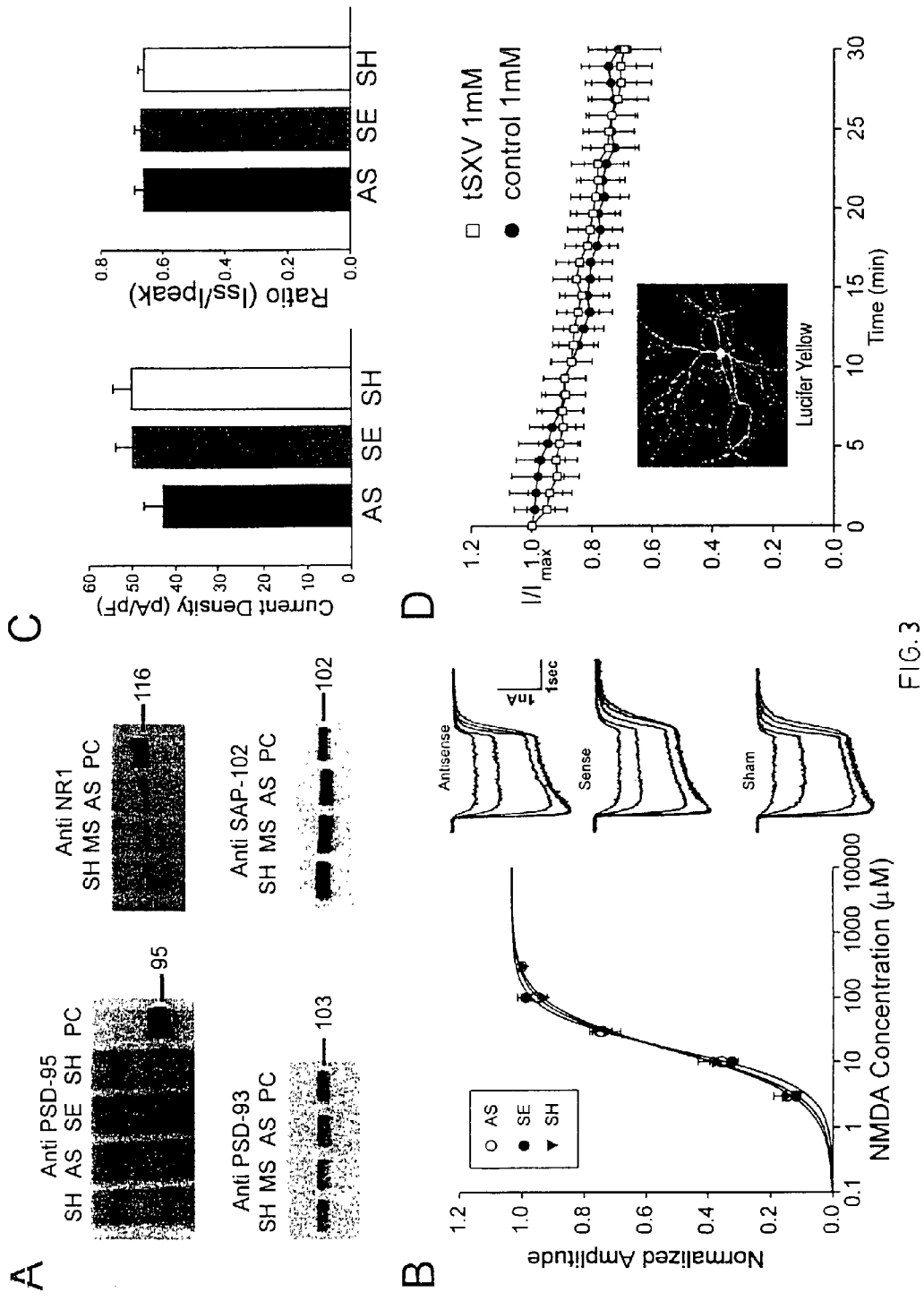
FIGS. 3a-d represent immunoblots (3a); NMDA dose-response curves (3b); NMDA current density measurements (3c); and current/time graph (3d) dialyzed with hucifer yellow.

FIG. 3, shows that there is no effect of perturbing PSD-95 on receptor function. A. Immunoblots of PSD-95 ODN-treated cultures probed for PSD-95, NR1, PSD-93, and SAP- 102 using specific antibodies. PC: positive control tissue from purified rat brain cell membranes. B. NMDA dose-response curves and representative NMDA currents (inset) obtained with 3-300 μM NMDA. C. NMDA current density measurements elicited with 300 μM NMDA (AS: n=18; SE: n=19; SH: n=17; one-way ANOVA F=1.10, p=0.34), and analysis of NMDA current desensitization. $I_{ss}$=steady-state current; $I_{peak}$=peak current. AS: n=15; SE: n=16; SH: n=16 (ANOVA, F=0.14, p=0.87). Time constants for current decay were AS: 1310±158 ms; SE, 1530±185 ms; SH: 1190±124 ms (ANOVA, F=1.22, p=0.31). D. Currents elicited with 300 μM NMDA in neurons dialyzed with LY (insert) and 1 mM tSXV or control peptide.

Figure 4:
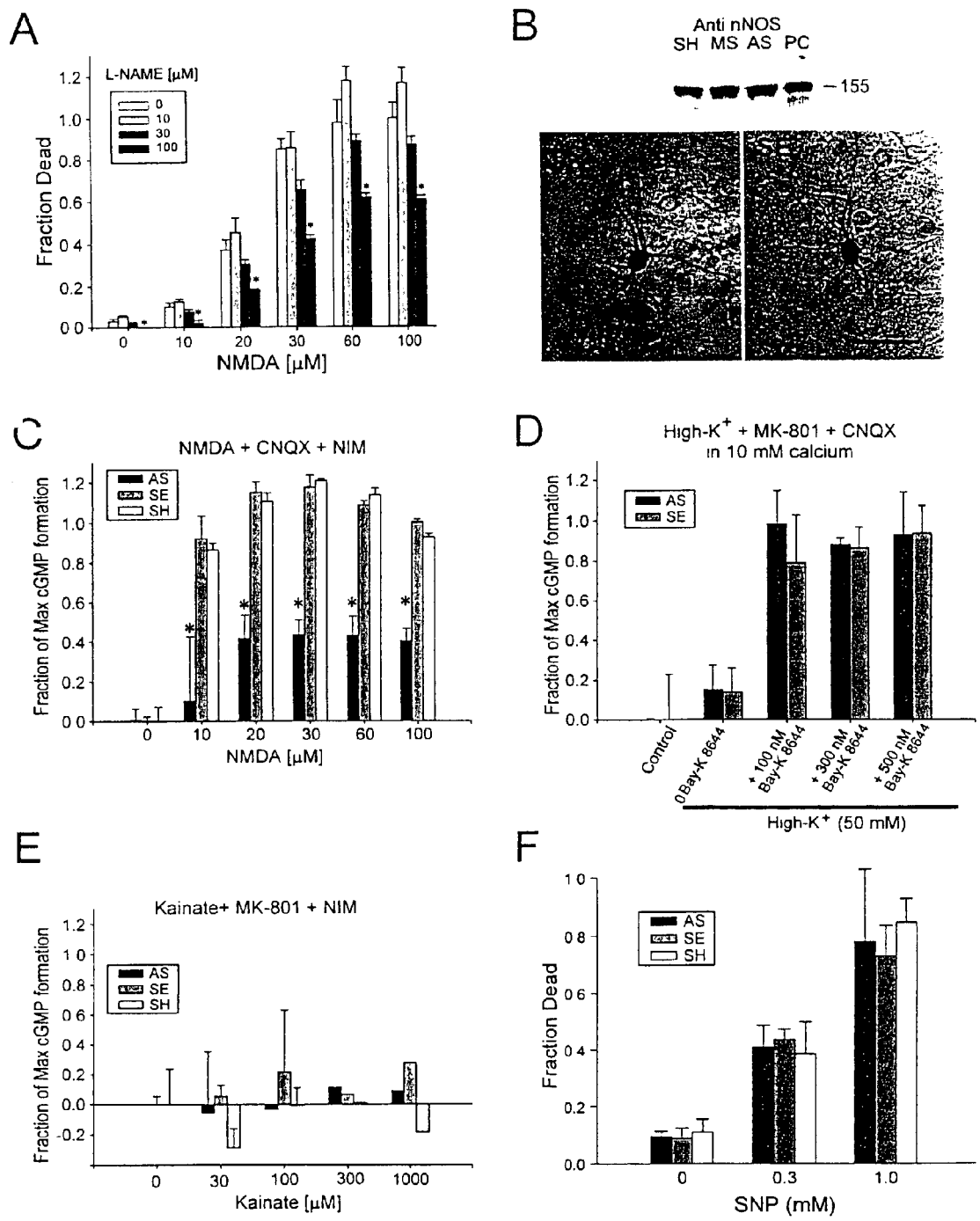
FIG. 4 bar charts (4a; 4c-4f) and immunoblot 4b of effect on nNOS expression in cultures are hereinafter better described and explained.

FIG. 4, shows the effect of coupling of NMDAR activation to nitric oxide signaling by PSD-95. A. L-NAME protects against NMDA toxicity (n=4, N=2). Asterisk: difference from 0 μM L-NAME (Bonferroni t-test, p<0.05). B. No effect of SH and of PSD-95 AS and MS ODNs on nNOS expression in cultures (immunoblot) and on NADPH diaphorase staining in PSD-95 AS and SE-treated neurons. PC: positive control tissue from purified rat brain cell membranes. C. Effect of isolated NMDAR activation on cGMP formation (n=12 cultures/bar pooled from N=3 separate experiments) D,E. Effects of VSCC activation (n=8/bar, N=2), and AMPA/kainate receptor activation (n=4/bar, N=1) on cGMP formation. Data in C-E are expressed as the fraction of cGMP produced in SE-treated cultures by 100 μM NMDA. Asterisk: differences from both SH and SE controls (Bonferroni t-test, p<0.0001). F. Sodium nitroprusside toxicity is similar in PSD-95 AS, SE and SH treated cultures.

PSD-95 expression was suppressed in cultured cortical neurons to <10% of control levels, using a 15-mer phosphodiester antisense (AS) oligodeoxynucleotide (ODN) (FIGS. 1A,B) Sham (SH) washes, sense (SE) and missense (MS) ODNs (9) had no effect. The ODNs had no effect on neuronal survivability and morphology as gauged by viability assays, herein below, and phase-contrast microscopy (not shown).

To examine the impact of PSD-95 on NMDAR-triggered excitotoxicity, ODN-treated cultures were exposed to NMDA (10-100 μM) for 60 min, washed, and either used for $^{45}Ca^{2+}$ accumulation measurements, or observed for a further 23 h. $Ca^{2+}$ influx was isolated to NMDARs by adding antagonists of non-NMDARs and $Ca^{2+}$ channels (4). NMDA toxicity was significantly reduced in neurons deficient in PSD-95 across a range of insult severities (FIGS. 1C,D; $EC_{50}$: AS: 43.2±4.3; SE: 26.3±3.4, Bonferroni t-test, p<0.005). Concomitantly however, PSD-95 deficiency had no effect on $Ca^{2+}$ loading into identically treated sister cultures (FIG. 1E). Therefore, PSD-95 deficiency induces resilience to NMDA toxicity despite maintained $Ca^{2+}$ loading.

I next examined whether the increased resilience to $Ca^{2+}$ loading in PSD-95 deficient neurons was specific to NMDARs. Non-NMDAR toxicity was produced using kainic acid (30-300 μM), a non-desensitizing AMPA/kainate receptor agonist (15), in the presence of NMDAR and $Ca^{2+}$ channel antagonists (4). Kainate toxicity was unaffected in PSD-95 deficient in neurons challenged for either 60 min (not shown) or 24 h (FIG. 2A1). Non-NMDAR toxicity occurred without significant $^{45}Ca^{2+}$ loading (FIG. 2A2), as >92% of neurons in these cultures express $Ca^{2+}$-impermeable AMPA receptors (4). However, $Ca^{2+}$ loading through VSCCs, which is non-toxic (4) (FIG. 2B1), was also unaffected by PSD-95 deficiency (FIG. 2B2). Thus, suppressing PSD-95 expression affects neither toxicity nor $Ca^{2+}$ fluxes triggered through pathways other than NMDARs.

Immunoblot analysis (11) of PSD-95 deficient cultures revealed no alterations in the expression of the essential NMDAR subunit NR1, nor of two other NMDAR-associated MAGUKs, PSD-93 and SAP-102 (FIG. 3A). This indicated that altered expression of NMDARs and their associated proteins was unlikely to explain reduced NMDA toxicity in PSD-95 deficiency (FIGS. 1C,D). Therefore, I examined the possibility that PSD-95 modulates NMDAR function. NMDA currents were recorded using the whole-cell patch technique (16) (FIG. 3B). PSD-95 deficiency had no effect on passive membrane properties, including input resistance and membrane capacitance [Capacitance: AS 55.0±2.6 pF (n=18 ); SE 52.7±3.2 pF (n=19); SH 48.1±3.4 pF (n=17; ANOVA, F=1.29, p=0.28)]. Whole-cell currents elicited with 3-300 μM NMDA were also unaffected. Peak currents were AS: 2340±255 pA (n=18); SE: 2630±276 (n=19); SH: 2370±223 (n=17) (FIG. 3B, inset; one-way ANOVA, F=0.43, p=0.65). NMDA dose-response relationships also remained unchanged (FIG. 3B; $EC_{50}$ AS: 16.1±0.8 μM (n=7); SE: 15.5±2.1 (n=6); SH: 15.9±2.9; one-way ANOVA, F=0.02, p=0.98), as were NMDA current density and desensitization (FIG. 3C).

To further examine the effect of PSD-95 binding on NMDAR function, a 9 aa peptide, KLSSIESDV (SEQ ID NO: 1) corresponding to the C-terminal domain of the NR2B subunit characterized by the tSXV motif (6) was injected into the neurons. At 0.5 mM, this peptide competitively inhibited the binding of PSD-95 to GST-NR2B fusion proteins (6), and was therefore predicted to uncouple NMDARs from PSD-95. Intracellular dialysis of 1 mM tSXV or control peptide, CSKDTMEKSESL (SEQ ID NO: 3) (6) was achieved through patch pipettes (3-5 MΩ) also containing the fluorescent tracer Lucifer Yellow (LY). This had no effect on NMDA currents over 30 min despite extensive dialysis of LY into the cell soma and dendrites (FIG. 3D). Peak current amplitudes were tSXV: 2660±257 pA (n=9), control: 2540±281 pA (n=10; $t_{(17)}$=0.31, p=0.76).

The data is consistent with that obtained from recently generated mutant mice expressing a truncated 40K PSD-95 protein that exhibited enhanced LTP and impaired learning (17). Hippocampal CA1 neurons in PSD-95 mutants exhibited no changes in NMDAR subunit expression and stoichiometry, cell density, dendritic cytoarchitecture, synaptic morphology, or NMDAR localization using NR1 immunogold labeling of asymmetric synapses. NMDA currents, including synaptic currents, were also unchanged (16). I also found no effects of PSD-95 deficiency on NMDAR expression, on other NMDAR associated MAGUKs, nor on NMDA-evoked currents. In addition, NMDAR function gauged by measuring NMDA-evoked $^{45}Ca^{2+}$-accumulation was unaffected. Thus, the neuroprotective consequences of PSD-95 deficiency must be due to events downstream from NMDAR activation, rather than to altered NMDAR function.

The second PDZ domain of PSD-95 binds to the C-terminus of NR2 subunits and to other intracellular proteins (8). Among these is nNOS (18), an enzyme that catalyzes the production of nitric oxide (NO), a short-lived signaling molecule that also mediates $Ca^{2+}$-dependent NMDA toxicity in cortical neurons (12). Although never demonstrated experimentally, the NMDAR/PSD-95/nNOS complex was postulated to account for the preferential production of NO by NMDARs over other pathways (8). To determine whether NO signaling plays a role in NMDA toxicity in the present cultures, we treated the cells with $N^G$-nitro-L-arginine methyl ester (L-NAME), a NOS inhibitor (12). L-NAME protected the neurons against NMDA toxicity (FIG. 4A), indicating the possibility that suppressing PSD-95 might perturb this toxic signaling pathway.

The effect of suppressing PSD-95 expression on NO signaling and toxicity was examined using cGMP formation as a surrogate measure of NO production by $Ca^{2+}$-activated nNOS (20,21). PSD-95 deficiency had no impact on nNOS expression (FIG. 4B), nor on the morphology (FIG. 4B) or counts of NADPH diaphorase-staining (12) neurons (SH: 361±60, SE: 354±54, AS: 332±42 staining neurons/10 mm coverslip, 3 coverslips/group). However, in neurons lacking PSD-95 challenged with NMDA under conditions that isolated $Ca^{2+}$ influx to NMDARs (4), cGMP production was markedly attenuated (>60%; FIG. 4C, one-way ANOVA, p<0.0001). Like inhibited toxicity (FIGS. 1,2), inhibited cGMP formation in neurons lacking PSD-95 was only observed in response to NMDA. It was unaffected in neurons loaded with $Ca^{2+}$ through VSCCs (FIG. 4D), even under high neuronal $Ca^{2+}$ loads matching those attained by activating NMDARs (compare FIGS. 1E and 2B2) (4). nNOS function therefore, was unaffected by PSD-95 deficiency. AMPA/kainate receptor activation failed to load the cells with $Ca^{2+}$ (FIG. 2A2), and thus failed to increase cGMP levels (FIG. 4E). Our findings indicate that suppressing PSD-95 selectively reduces NO production efficiency by NMDAR-mediated $Ca^{2+}$ influx, but preserves NO production by $Ca^{2+}$ influx through other pathways.

Bypassing nNOS activation with NO donors restored toxicity in neurons lacking PSD-95. The NO donors sodium nitroprusside (12) (FIG. 4F; $EC_{50}$ 300 µM) and S-nitrosocysteine (17) (not shown) were highly toxic, irrespective of PSD-95 deficiency. Thus, reduced NMDA toxicity in PSD-95 deficient cells was unlikely to be caused by altered signaling events downstream from NO formation.

Suppressing PSD-95 expression uncoupled NO formation from NMDAR activation (FIG. 4C), and protected neurons against NMDAR toxicity (FIGS. 1C,D) without affecting receptor function (FIGS. 1E, 3A-D), by mechanisms downstream from NMDAR activation, and upstream from NO-mediated toxic events (FIG. 4F). Therefore, PSD-95 imparts NMDARs with signaling and neurotoxic specificity through the coupling of receptor activity to critical second messenger pathways. These results have broader consequences, as NMDAR activation and NO signaling are also critical to neuronal plasticity, learning, memory, and behavior (1,18, 19). Thus, these data provide experimental evidence for a mechanism by which PSD-95 protein may govern important physiological and pathological aspects of neuronal functioning.

Figure 5:
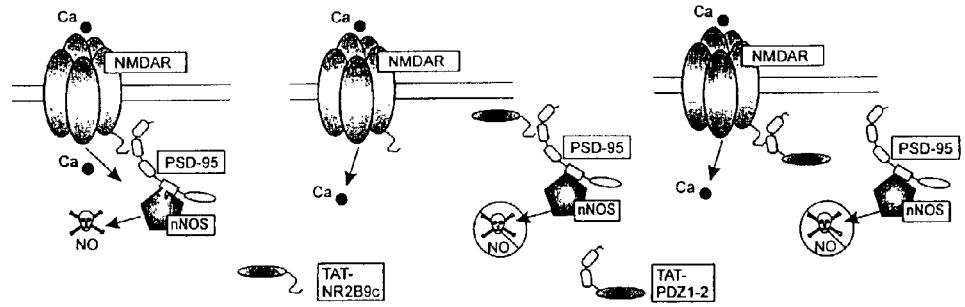
FIG. 5. (A) Shows the hypothesis: The NMDAR/PSD-95 complex may be dissociated by peptides encoding either to the C-terminus of NR2 or the second PDZ domains of PSD-95 (B) Fluorescence of cultures treated with Tat-38-48-dansyl and Tat-NR2B9c dansyl. (C) Time course fluorescence after Tat-NR2B9c-dansyl application (D) Effect of peptides on co-immunoprecipitation of PSD-95 with NR2B FIG. 6. Effect of Tat-NR2B9c on (A-C) electrophysiological function of neurons (D) NMDA-evoked $^{45}Ca^{2+}$ uptake in cortical cultures. (E) NMDA-evoked cGMP production in cortical cultures. (F) NMDA-evoked excitotoxicity in cortical cultures.
Figure 5:
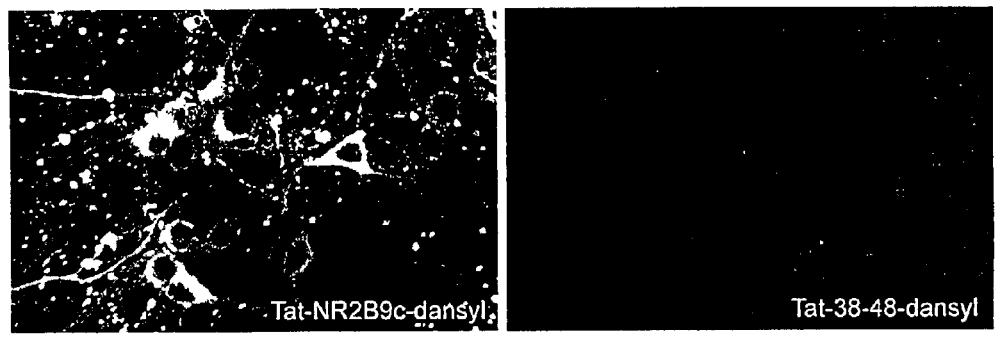
Figure 5:
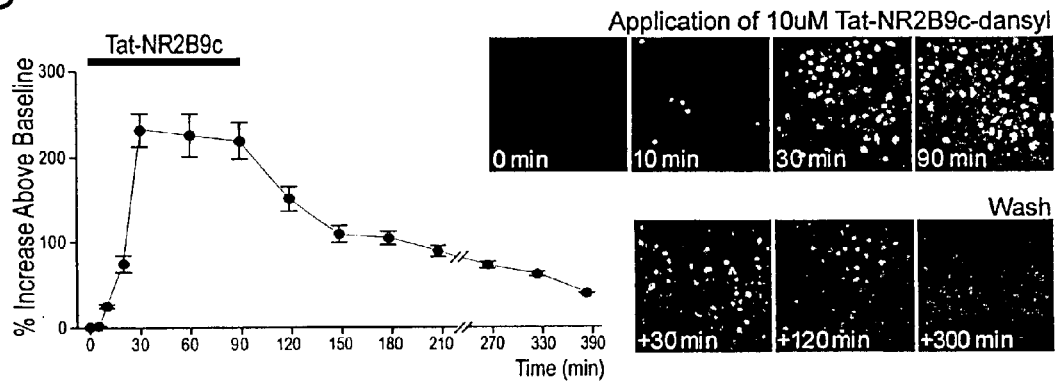
Figure 5:
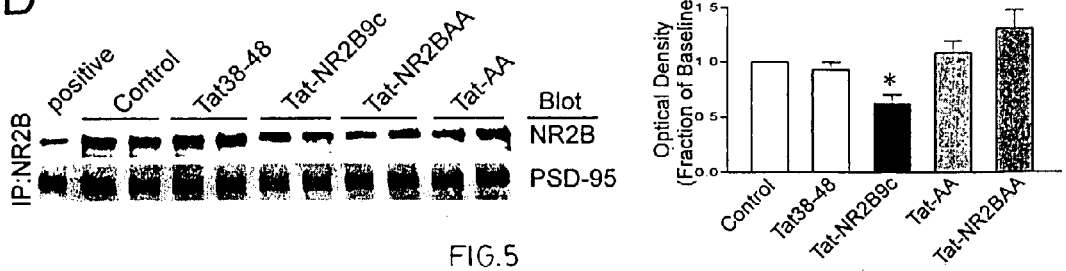

FIG. 5 shows the utility of Tat-peptides in dissociating the NMDAR/PSD-95 interaction (A) The hypothesis: The NMDAR/PSD-95 complex (left panel) may be dissociated using Tat peptides fused either to the C-terminus of NR2B (Tat-NR2B9c; middle) or to the first and second PDZ domains of PSD-95 (pTat-PDZ1-2; right), thus reducing the efficiency of excitotoxic signaling via $Ca^{2+}$-dependent signaling molecules (B) Intracellular accumulation of Tat-NR2B9c-dansyl (10 µM) but not control peptide (Tat-38-48-dansyl; 10 µM) was observed 30 min after application to cortical neuronal cultures using confocal microscopy (excitation: 360 nm, emission: >510 nm; representative of 5 experiments). Fluorescence of cultures treated with Tat-38-48-dansyl was similar to background (not shown). (C) Time course of Tat-NR2B9c-dansyl (10 µM) fluorescence after application to cortical cultures at room temperature (symbols: mean±S.E of 4 experiments. Inset: fluorescence images from representative experiment (D) Tat-NR2B9c, but not control peptides (see text), inhibits the co-immunoprecipitation of PSD-95 with NR2B in rat forebrain lysates (Left: Representative gel; Right: means±S.E of 4 experiments, ANOVA, F=6.086, *p=0.0041).

In more detail, a conserved tSXV motif at the C-terminus of the NR2B subunit is critical for binding to the PDZ2 domain of PSD-95. I hypothesized that interfering with this interaction might disrupt the coupling between NMDARs and PSD-95. This might be achieved by the intracellular introduction of exogenous peptides that bind to either the NR2B or the PDZ2 interaction domains (FIG. 5A). To this end I used a peptide comprised of the nine C-terminal residues of NR2B (KLSSIESDV; NR2B9c (SEQ ID NO: 1)), which is anticipated to bind the PDZ2 domain of PSD-95. As an alternative means to interfere with the NMDAR/PSD-95 interaction I constructed a protein comprised of residues 65-248 of PSD-95 encompassing the first and second PDZ domains (PDZ1-2), which contains the principal binding domain in PSD-95 for the C-terminus of NR2B. NR2B9c or PDZ1-2 on their own did not enter cells (not shown) and therefore, I fused each to a peptide corresponding to the cell-membrane transduction domain of the HIV-1-Tat protein (YGRKKRRQRRR (SEQ ID NO: 2); Tat) to obtain a 20 amino acid peptide (Tat-NR2B9c) and the fusion protein pTat-PDZ1-2. pTat-PDZ1-2 and pTat-GK fusion proteins were generated by insertion of PSD95 residues 65-248 encoding the PDZ 1 and 2, and residues 534-724 encoding the guanylate kinase-like domains, respectively, into pTAT-HA plasmids (generous gift of S. Dowdy, Washington University, St.Louis, Mo.). Fusion proteins contain a 6X His-tag, the protein transduction domain of HIV-1 Tat and a hemagglutinin-tag N-terminal to the insert. Plasmids were transformed into BL21(DE3)LysS bacteria (Invitrogen) and recombinant proteins were isolated under denaturing conditions on a Nickle-His column (Amersham-Pharmacia). These are anticipated to transduce cell membranes in a rapid, dose-dependent manner independent of receptors and transporters (30).

To determine whether Tat-NR2B9c was able to transduce into neurons, I conjugated the fluorophore dansyl chloride to Tat-NR2B9c and to a control peptide comprised of HIV-1-Tat residues 38-48 (KALGISYGRKK (SEQ ID NO: 4); Tat38-48) outside the Tat transduction domain (31).

Electrophysiological Recordings were made in 400 µm Hippocampal slices from 20-36 day old Sprague-Dawley rats perfused at room temperature with ACSF containing (in mM) 126 NaCl, 3 KCl, 2 $MgCl_2$, 2 $CaCl_2$, 1.2 $KH_2PO_4$, 26 $NaHCO_3$ and 10 glucose and bubbled with 95%$O_2$/5%$CO_2$. Whole-cell recordings of CA1 neurons were performed using the "blind" method with an Axopatch-1D amplifier (Axon Instruments, Foster City, Calif.) at holding potential –60 mV. Pipettes (4-5 MΩ) were filled with solution containing (mM): 135 CsCl, 2 $MgCl_2$, 0.1 $CaCl_2$, 0.5 EGTA, 10 HEPES, 4 Mg-ATP, 0.2 GTP, and 5 QX-314, pH 7.4, 310 mOsm. Field potentials were recorded with glass micropipettes (2-4 MΩ) filled with ACSF placed in the stratum radiatum 60-80 µm from the cell body layer. Synaptic responses were evoked by stimulation (0.05 ms) of the Schaffer collateral-commissural pathway with a bipolar tungsten electrode in the presence of bicuculline methiodide (10 µM). For $I_{NMDA}$ recording, $Mg^{2+}$ was removed from and 20 µM CNQX was added in ACSF. Following 10-20 min base line recordings of EPSCs, $I_{NMDA}$ and fEPSPs, Tat-peptides were applied in ACSF and recordings were continued for 30 min thereafter.

I bath applied these to cultured cortical neurons and observed their fluorescence by confocal microscopy. Neurons treated with Tat-NR2B9c-dansyl (10 µM) exhibited fluorescence in their cytoplasm and processes, indicating intracellular peptide delivery (FIG. 5B, left). Sister cultures treated with Tat38-48-dansyl (10 µM) exhibited only background fluorescence, indicating no observable peptide uptake in the absence of the Tat transduction domain (FIG. 5B, right). Tat-NR2B9c-dansyl was detectable in the neurons within 10 min of the start of the application and the peptide accumulated to a maximum level over the next 20 min (FIG. 5C). This level was maintained until the dansyl-Tat-NR2B9c was washed from the bath and the peptide remained detectable within the neurons for more than 5 hours thereafter. Therefore, the Tat transduction domain was able to act as a carrier for NR2B9c and the Tat-NR2B9c fusion peptide remained in neurons for many hours after being applied extracellularly.

To determine whether Tat-NR2B9c may disrupt the interaction between NMDARs and PSD-95 I made use of rat brain proteins prepared under weakly denaturing conditions known to permit the NMDAR/PSD-95 interaction. Adult (7-8W) wistar rat forebrains were removed and homogenized in ice-cold buffer (0.32M Sucrose, 0.1 mM Na3VO4, 0.1 mM PMSF, 0.02M PNPP, 0.02M glycerol phosphate, and 5 ug/ml each of antipain, aprotinin, and leupeptin). Homogenates were centrifuged at 800 gr for 10 min at 4.degree. C. The supernatants were combned and centrifuged at 11,000 g at 4 degree for 20 min and the pellet (P2) was resuspended in homogenization buffer. P2 membranes were adjusted 200 ug protein190 ul with homogenization buffer with a final concentration of 1% DOC and 0.1% Triton X-100. The proteins were incubated with Tat-NR2B9c or with one of three controls: Tat38-48, the Tat transduction sequence conjugated to two alanine residues (Tat-AA), or a Tat-NR2B9c peptide in which the C-terminal tSXV motif contained a double point mutation (Tat-KLSSIEADA [SEQ ID NO: 5]; Tat-NR2BAA) rendering it incapable of binding PSD-95. I immunoprecipitated NMDARs, together with associated proteins, with an antibody that selectively recognizes NR2B. The proteins were separated by SDS-PAGE and probed with anti-PSD-95 or anti-NR2B antibodies.sup. 16 NR2B was precipitated from rat forebrain extracts using a polyclonal rabbit anti-NR2B antibody generated against the C-terminal region encompassing amino acid residues 935-1,455 of the NR2B protein. Proteins were then separated on 8% SDS-PAGE gels and probed with monoclonal anti-NR2B (Clone 13, Transduction Laboratories) or anti PSD-95 antibodies (Clone 7E3-1B8, Affinity Bioreagents.Inc). Detection of proteins was achieved using HRP-conjugated secondary antibodies and enhanced chemiluminescence. I found that Tat-NR2B9c reduced the co-immunoprecipitation of PSD-95 with NR2B. On average the optical density signal was reduced by 37.6.+−.8.2% as compared with controls (FIG. 5D). In contrast, none of the three control peptides reduced the co-immmunoprecipitation of PSD-95 with NR2B. Thus, I conclude that Tat-NR2B9c disrupts the interaction between NMDARs and PSD-95 and that this is dependent upon an intact PDZ binding motif in the peptide.

Figure 6:
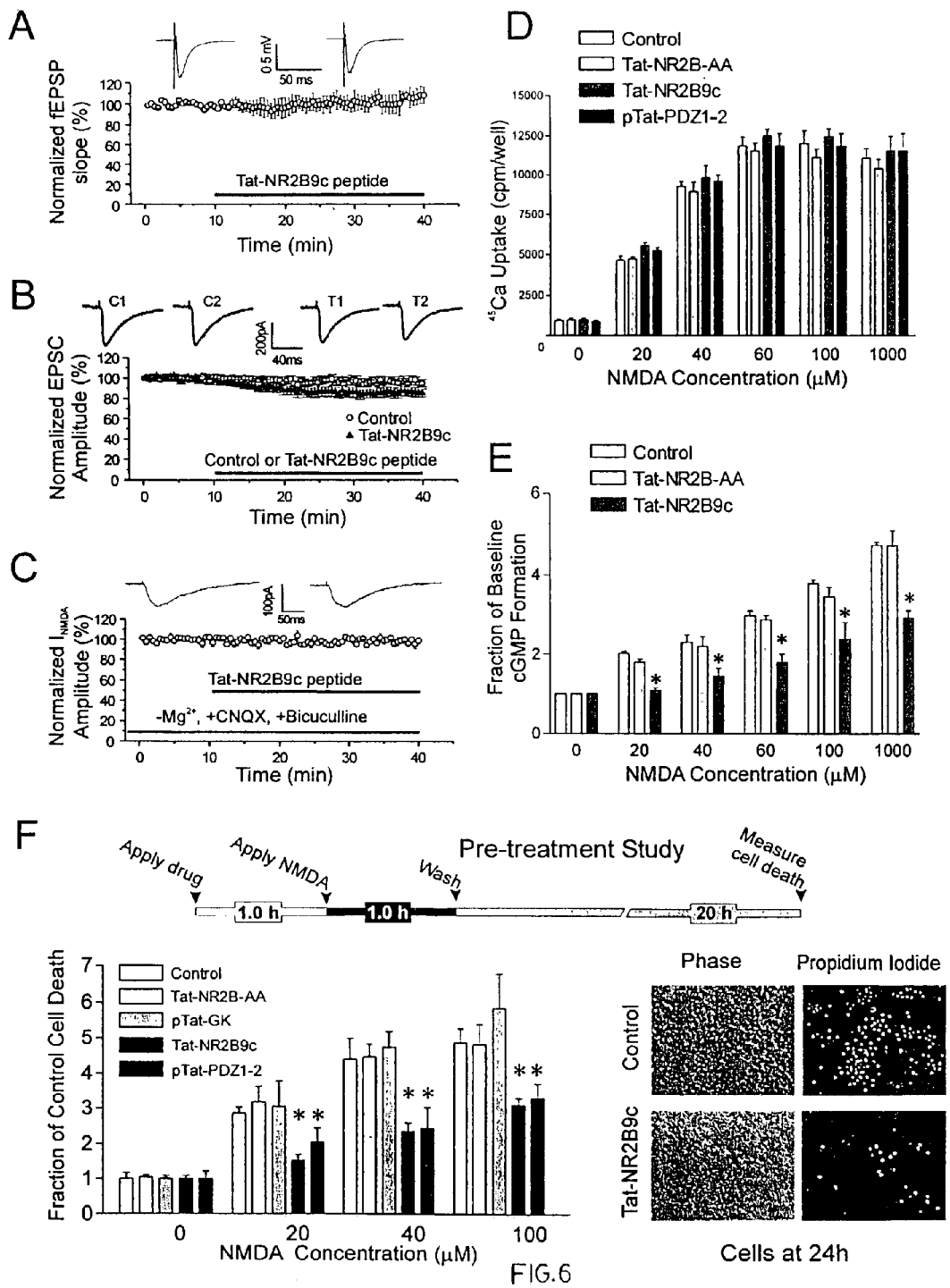

FIG. 6 shows neuroprotection and reduction of NO signaling by Tat-peptides without affecting NMDAR function (A) Effect of Tat-NR2B9c (50 nM) on field excitatory post-synaptic currents (fEPSC) in CA1 neurons in acute hippocampal slices. (B) Effect of 50 nM Tat-NR2B9c or Tat-38-48 (control) on whole-cell excitatory post synaptic currents (EPSC). (C) Effect of Tat-NR2B9c on the NMDA component of the EPSC isolated pharmacologically by applying the AMPAR antagonist CNQX, and concomitant removal of extracellular $Mg^{2+}$. (D) Effect of 50 nM Tat-NR2B9c treatment on NMDA-evoked $^{45}Ca^{2+}$ uptake in cortical cultures. Tat-peptides were bath-applied 1 h prior to the NMDA application. (E) Effect of 50 nM Tat-NR2B9c treatment on NMDA-evoked cGMP production in cortical cultures. Asterisk: differences from control and Tat-NR2B-AA at each NMDA concentration (Bonferroni t-test, p<0.01). (F) Decreased excitotoxicity at 20 h at all NMDA concentrations in cultured cortical neurons pre-treated with 50 nM Tat-NR2B9c or pTat-PDZ1-2 for 1 h. Asterisk: differences from control, Tat-NR2B-AA and pTat-GK at each NMDA concentration (Bonferroni t-test, p<0.005). Right panels: Representative phase contrast and propodium iodide fluorescence images of cultures 20 h after challenge with 100 µM NMDA with and without Tat-NR2B9c treatment. Bars in (D), (E) and (F) indicate the mean±S.E. for 12 cultures in 3 separate experiments.

In more detail, as NMDAR-mediated synaptic responses are not altered by the loss of PSD-95 (24) I predicted that Tat-NR2B9c would not affect the function of NMDARs. This was tested by examining the effect of Tat-NR2B9c on NMDAR-mediated currents and on NMDA-evoked uptake of $^{45}Ca^{2+}$. Bath-applying Tat-NR2B9c (50 nM) to acute rat hippocampal slices had no effect on synaptic responses of CA1 neurons evoked by stimulation of the Schaffer collateral-commissural pathway (FIG. 6A) nor on patch recordings of the total excitatory post-synaptic currents (EPSC) recorded in CA1 neurons, (FIG. 6B) nor on the pharmacologically isolated AMPA (not shown) or NMDA components of the EPSC (FIG. 6C). Moreover, using cortical cultures I found that pre-treating cultures with Tat-NR2B9c or with pTat-PDZ1-2 (each at 50 nM) did not alter the uptake of $^{45}Ca^{2+}$ produced by applying NMDA (FIG. 6D); CNQX (10 µM) and nimodipine (2 µM) were present in the extracellular solution in these and all subsequent experiments using cultured neurons so as to isolate signaling and thereby preventing secondary activation of AMPARs or of voltage-gated $Ca^{2+}$ channels, respectively (25,32,33).

As the function of NMDARs was unaffected by administering Tat-NR2B9c, I next determined whether this peptide altered signaling events downstream of NMDAR activation. To this end I examined stimulation of nNOS, as a key downstream signaling enzyme that mediates the neurotoxic effects of NMDAR activation[5]. I measured NMDA-evoked changes in the levels of guanosine 3',5'-monophosphate (cGMP) as a surrogate measure of NO production by NMDAR stimulated nNOS activity[7,20]. Cultured cortical neurons were pre-treated for 1 h with Tat-NR2B9c (50 nM), the non-interacting Tat-NR2B-AA (50 nM) or with sham washes and challenged with NMDA (0-1000 µM) in the presence of CNQX and nimodipine as above. NMDA produced a concentration-dependent increase in cGMP that was significantly suppressed (average of 39.5±6.7%) by pre-treating the cultures with Tat-NR2B9c (FIG. 6E). In contrast, NMDAR-stimulated elevation of cGMP was unaffected by pre-treatment with Tat-NR2B-AA. Thus, Tat-NR2B9c, but not a mutant peptide incapable of interacting with PSD-95, depressed NMDAR-evoked stimulation of NO-cGMP signaling.

Although Tat-NR2B9c and pTat-PDZ1-2 did not affect NMDAR function, Tat-NR2B9c was shown to interfere with NMDAR/PSD-95 binding and to suppress downstream NO signaling. Thus, I predicted that Tat-peptide treatment should enhance neurons' resilience to NMDA toxicity. To test this I pre-treated cortical neuronal cultures with Tat-peptides (50 nM) for 1 h, then applied NMDA (0-100 µM) for 1 h followed by a 20 h observation period (FIG. 6F, inset). Control neurons were treated with sham washes, or with the non-interacting control Tat-NR2BAA. In cultures treated with Tat-NR2B9c, cell death was significantly reduced at all concentrations tested (FIG. 6F) whereas pre-treatment with Tat-NR2B-AA had no effect on cell death. Thus, NMDAR-stimulated neurotoxicity is suppressed by pre-treatment with Tat-NR2B9c, suppression that is lost by mutating the PSD-95 binding region of the peptide.

If Tat-NR2B9c suppresses NMDA excitotoxicity by interfering with the binding of NR2B to PSD-95 then interfering with this binding by an alternative means should also suppress the toxicity. I tested pTat-PDZ1-2, predicted to interfere with PSD-95 binding to NR2B and which permeates into the cells (not shown), though without effect on NMDA-evoked $Ca^{2+}$ accumulation (FIG. 6D). Pre-treating the cultures with pTat-PDZ1-2 attenuated the neurotoxicity of NMDA to a similar degree as Tat-NR2B9c (FIG. 6F). As a control, I made and used pTat-GK, a Tat fusion protein containing residues 534-724 of PSD-95 comprising the carboxyl-terminal guanylate-kinase homology domain that lacks enzymatic activity[21]. pTat-GK, which is devoid of the necessary domains to bind NR2B, had no effect on the NMDA-evoked cell death (FIG. 6F). Thus, interfering with the NMDAR/PSD-95 interaction using peptides that target either side of the interaction reduces in vitro excitotoxicity produced by NMDAR activation.

Figure 7:
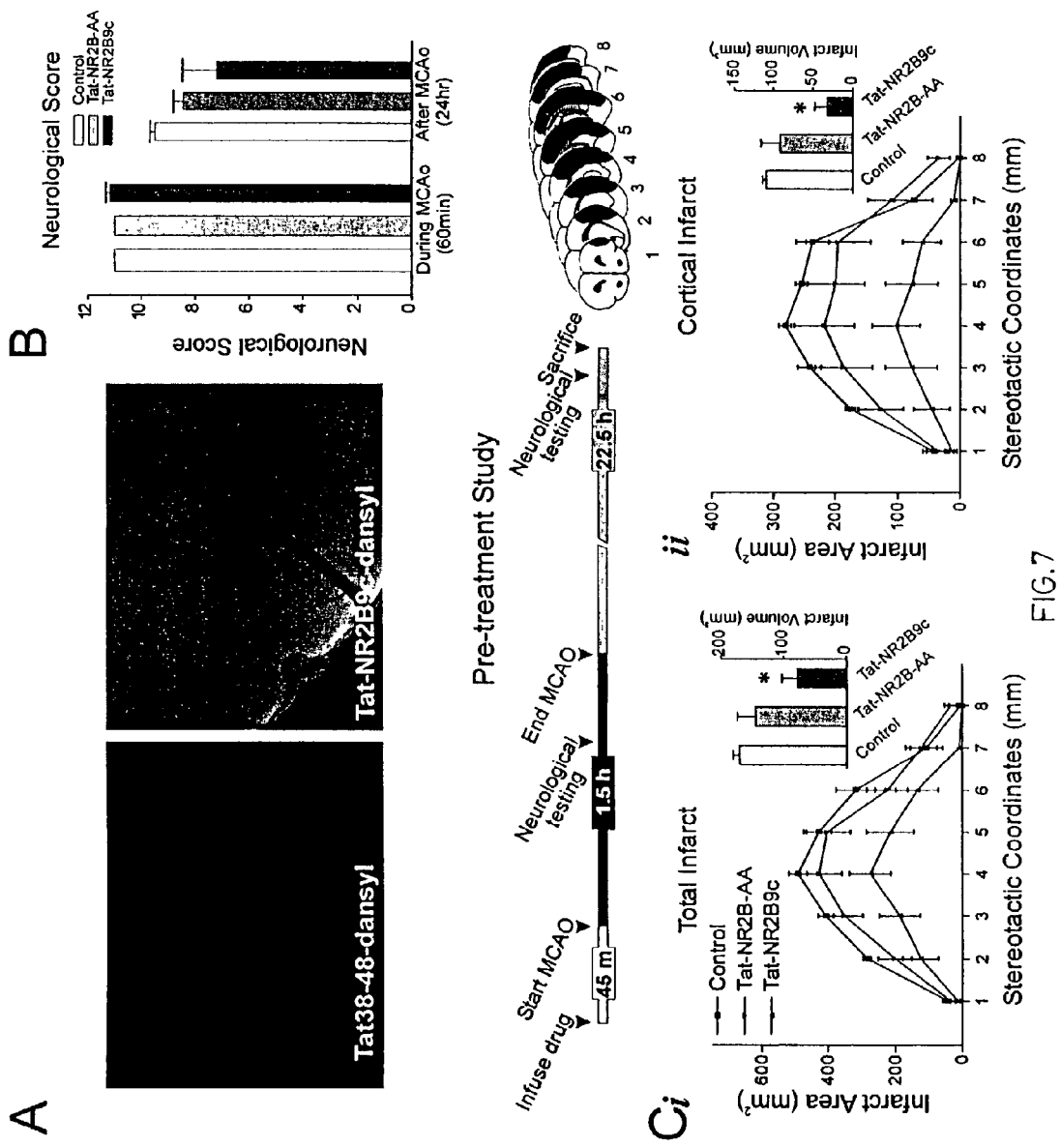
FIG. 7. (A) Detection of Tat-NR2B9c-dansyl in the mouse brain 1 h after intraperitoneal injection (B) Composite neurological scores (see text) during and 24 h after MCAo. (C) Effect of Pre-treatment with Tat-NR2B9c on (i) total infarct area and volume (inset), and (ii) cortical infarct area and volume (inset) after transient MCAo.

FIG. 7 shows neuroprotection by Tat-NR2B9c pretreatment in-vivo. (A) Detection of Tat-NR2B9c-dansyl but not Tat38-48-dansyl in the cortex of C57BL/6 mouse brain 1 h after intraperitoneal injection (0.5 μmole total dose). Fluorescence of brains from animals treated with Tat-38-48-dansyl was similar to background (not shown). (B) Composite neurological scores (see text) during and 24 h after MCAo. (C) Pre-treatment with 3 nmole/g Tat-NR2B9c but not mutated Tat-NR2B-AA or saline (control) significantly reduced (i) total infarct area and volume (inset), ANOVA; F=7.3, p<0.005 and (ii) cortical infarct area and volume (inset), ANOVA; F=8.35, p<0.005 measured 24 h after transient MCAo. (n=6 animals per group; symbols and bars indicate mean±S.E). Infarct volume was calculated by analyzing the infarct area in 8 stereotactic coordinates of the brain as shown at right inset.

Agents that block NMDAR activity were initially deemed as promising neuroprotectants for stroke and other neurological disorders involving excitotoxic mechanisms, but were later shown to be deleterious or ineffective in animal and human studies (27,28,29). However, Tat-peptides that target the NMDAR/PSD-95 interaction protect against NMDA toxicity without blocking NMDARs. Therefore I reasoned that treatment with Tat-NR2B9c in vivo could serve as an improvement on NMDA blockers in the treatment of ischemic brain damage.

Before testing this I determined whether Tat-NR2B9c could be delivered into the brain in the intact animal. I injected 25 g C57BL/6 mice intraperitoneally with a 500 μmole dose of either Tat-NR2B9c-dansyl, or with Tat38-48-dansyl as a non-transducing control. 40 μm cryostat coronal brain sections taken 1 h after injection[22] were examined for peptide uptake using dansyl fluorescence detection by confocal microscopy. The mice were perfused with fixative solution (3% paraformaldehyde, 0.25% glutaraldehyde, 10% sucrose, 10 U/mL heparin in Saline) 1 hour after peptide injection. Brains were removed, frozen in 2-methylbutane at −42° C. and 40□ m sections were cut using a Leitz Kryostat. Brain sections from animals injected with Tat-NR2B9c exhibited strong fluorescence in the cortex (FIG. 7A, right), and in all other areas examined (hippocampus, striatum; not shown), whereas signal from controls remained at background levels (FIG. 7A, left). Similar results were obtained using intravenous injection in rats (not shown). Thus, Tat-NR2B9c enters the brain upon peripheral administration.

Next, I examined whether pretreatment with Tat-peptides would reduce stroke damage. Experiments were carried out in adult male Sprague-Dawley rats subjected to transient middle cerebral artery occlusion (MCAO) for 90 minutes by the intraluminal suture method (36,37). Animals were fasted overnight and injected with atropine sulfate (0.5 mg/kg IP). After 10 minutes anesthesia was induced with 3.5% halothane in a mixture of nitrous oxide and oxygen (Vol. 2:1) and maintained with 0.8% halothane. Rats were orally intubated, mechanically ventilated, and paralyzed with pancuronium bromide (0.6 mg/kg IV). Body temperature was maintained at 36.5-37.5° C. with a heating lamp. Polyethylene catheters in the femoral artery and vein were used to continuously record blood pressure and to sample blood for gas and pH measurements. Transient MCAO was achieved for 90 min by introducing a poly-L-lysine-coated 3-0 monofilament nylon suture (Harvard Apparatus) into the circle of Willis via the internal carotid artery, effectively occluding the middle cerebral artery. This produces an extensive infarction encompassing the cerebral cortex and basal ganglia. Animals were pretreated with either saline, the Tat-NR2B-AA control, or with Tat-NR2B9c by a single intravenous bolus injection 45 min prior to MCAO (3 nMoles/g). Physiological parameters (body temperature, blood pressure, blood gases) were monitored and maintained throughout the experiment (Table 1). All experimental manipulations and analyses of data were performed by individuals blinded to the treatment groups. The extent of cerebral infarction was measured 24 h after MCAO onset (FIG. 7C inset). The postural reflex test (38), and the forelimb placing test (39) were used to grade neurological function on a scale of 0 to 12 (normal=0; worst=12) during MCAO (at 50 minutes) and 24 h thereafter.

Pretreatment with Tat-NR2B9c produced a trend toward improvement in 24 h neurological scores in animals treated with Tat-NR2B9c (FIG. 7B). Moreover, the treatment reduced the volume of total cerebral infarction by 54.6±11.27% as compared with stroke volume in controls (FIG. $7C_i$; ANOVA, F=7.289, p=0.0048). This effect was largely accounted-for by a 70.7±11.23% reduction in cortical infarction (FIG. $7C_{ii}$, ANOVA, F=8.354, p=0.0027), which is thought to be largely caused by NMDAR-dependent mechanisms.

A treatment for stroke with a single-bolus drug injection would be most therapeutically valuable if effective when given after the onset of ischemia. I thus first evaluated whether treatment with Tat-peptides could be neuroprotective when applied post-insult in vitro.

Figure 8:
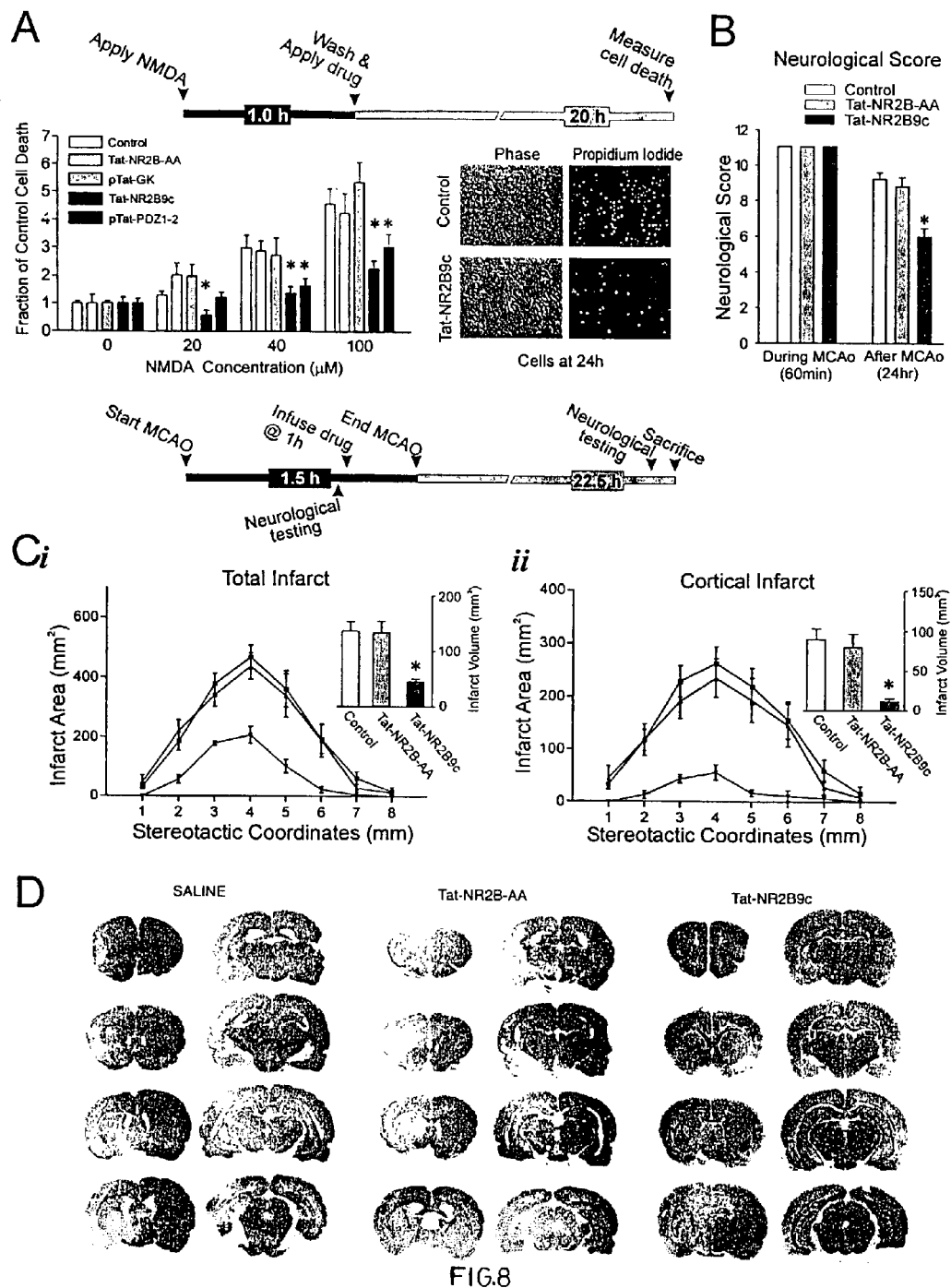
FIG. 8. (A) Neuroprotective effects of post-treatment in cultured cortical neurons post-treated with Tat-NR2B9c or pTat-PDZ1-2 (B) Composite neurological scores (see text) during and 24 h after MCAo. (C) Effect of post-treatment with Tat-NR2B9c on (i) total infarct area and volume (inset), and (ii) cortical infarct area and volume (inset) after transient MCAo.

FIG. 8 shows neuroprotection by post-treatment with Tat-NR2B9c in-vitro and in-vivo (A) Decreased excitotoxicity at 20 h in cultured cortical neurons post-treated with 50 nM Tat-NR2B9c or pTat-PDZ1-2 at 1 h after NMDA application. Bars indicate the mean±S.E. for 12 cultures in 3 separate experiments. Asterisk: differences from control, Tat-NR2B-AA and pTat-GK at each NMDA concentration (Bonferroni t-test, p<0.005). Right panels: Representative phase contrast and propodium iodide fluorescence images of cultures 24 h after challenge with 100 μM NMDA with and without Tat-NR2B9c treatment. (B) Composite neurological scores (see text) during and 24 h after MCAo. Asterisk: difference from control and Tat-NR2B-AA (ANOVA; F=17.25, p<0.0001). (C) Post-treatment with 3 nmole/g Tat-NR2B9c (9 animals) but not mutated Tat-NR2B-AA (8 animals) or saline controls (10 rats) significantly reduced (i) total infarct area and volume (inset), ANOVA; F=12.0, p<0.0005 and (ii) cortical infarct area and volume (inset), ANOVA; F=12.64, p=0.0001 as measured 24 h after transient MCAo. Symbols and bars indicate mean±S.E (D). Representative appearance of H&E stained rat brain sections from which the infarct areas were analyzed.

Cultured cortical neurons were exposed to an NMDA challenge (0-100 µM) for 1 h and were then treated with the Tat-peptides (all at 50 nM) described in the pre-treatment study (FIG. 6F). Cell death was gauged 20 h thereafter (FIG. 8A—inset). Post-treatment with Tat-NR2B9c or with pTat-PDZ1-2 significantly reduced the vulnerability of neurons to NMDA toxicity as compared with control cultures post-treated with sham washes, with Tat-NR2BAA, or with pTat-GK (FIG. 8A). Thus, when administered 1 hr after the start of the NMDA insult each of the Tat fusion constructs that target the NMDAR/PSD-95 interaction significantly reduced neuronal cell death in vitro.

Finally, I examined whether treatment with Tat-NR2B9c could attenuate ischemic neuronal damage in-vivo when given after stroke onset. A post-treatment study was conducted in which the rats were subjected to transient MCAO for 90 minutes as before, but the intravenous saline or Tat-peptide bolus (Tat-NR2B9c or Tat-NR2B-AA; 3 nMole/g) was injected 1 h after MCAO onset (FIG. 8C—inset). Infarction volume and neurological outcome measurements were performed at times identical to the pre-treatment study. Body temperature, blood pressure and blood gases were monitored throughout the 24 h experiment and maintained equivalent between groups (Table 2).

Post-treatment with Tat-NR2B9c, but not with Tat-NR2B-AA or saline, resulted in animals exhibiting a significant improvement in 24 h neurological scores as compared with controls (FIG. 8B; ANOVA, F=17.25, p<0.0001). Most strikingly, post-treatment with Tat-NR2B9c reduced the volume of total cerebral infarction by 67.0±3.75% as compared with stroke volume in controls (FIG. $8C_i$; ANOVA, F=11.99, p=0.0002). Similar to the previous study, this reduction was accounted-for by a 86.97±4.38% reduction in cortical infarction volume (FIG. $8C_{ii}$, 4D; ANOVA, F=12.64, p<0.0001).

The aforesaid description demonstrates that introducing into cells an exogenous peptide containing the C-terminal nine amino acids of the NR2B NMDAR subunit has profound effects on signaling pathways downstream of NMDAR activation, on in vitro excitotoxicity, and on in vivo ischemic brain damage. The effects of this peptide are lost by mutating amino acids that are essential for mediating PDZ binding to PSD-95. In addition, a protein comprising PDZ1-2 of PSD-95 shares the effects of the NR2B C-terminal peptide. Together these findings imply that the downstream signaling from NMDARs that leads to negative consequences for neuronal viability may be interrupted by interfering with the interaction between NR2B and PSD-95.

I have discovered that the strategy of treating neurons with Tat-fusion peptides is effective in reducing vulnerability to excitotoxicity in vitro and stroke damage in vivo. As this occurs without affecting NMDAR activity then adverse consequences of blocking NMDARs are not expected. Efficacy after the insult onset suggests that targeting the NMDAR/PSD-95 interaction is a practical future strategy for treating stroke. It is also likely that targeting other intracellular proteins using the same approach could be used to modulate additional signaling mechanisms mediated by protein-protein interactions that lead to other human diseases.

TABLE 1

Physiological Variables in Pre-Treatment MCAO Study

| Physiological Variables | Control (n = 6) | TAT-NR2BAA (n = 6) | TAT-NR2B9c (n = 6) |
| --- | --- | --- | --- |
| Before anesthesia | | | |
| Body weight, g | 269 ± 6 | 273 ± 7 | 271 ± 5 |
| Before MCAo (45 min) | | | |
| Body Temperature, ° C. | 36.7 ± 0.07 | 36.7 ± 0.17 | 36.6 ± 0.21 |
| MABP, mmHg | 119 ± 4 | 115 ± 5 | 120 ± 9 |
| Before MCAo (30 min) | | | |
| Body Temperature, ° C. | 36.8 ± 0.08 | 36.5 ± 0.12 | 36.7 ± 0.19 |
| MABP, mmHg | 107 ± 3 | 110 ± 4 | 76 ± 5* |
| Blood gases | | | |
| PH | 7.44 ± 0.02 | 7.44 ± 0.02 | 7.44 ± 0.02 |
| PO2, mmHg | 104 ± 3 | 110 ± 7 | 123 ± 8 |
| PCO2, mmHg | 39.6 ± 1.3 | 39.1 ± 1.4 | 38.1 ± 1.4 |
| Before MCAo (15 min) | | | |
| Body Temperature, ° C. | 36.9 ± 0.11 | 36.6 ± 0.15 | 36.7 ± 0.20 |
| MABP, mmHg | 111 ± 6 | 115 ± 5 | 90 ± 6* |
| During MCAo (5 min) | | | |
| Body Temperature, ° C. | 36.9 ± 0.03 | 36.6 ± 0.17 | 36.7 ± 0.16 |
| MABP, mmHg | 132 ± 6 | 135 ± 7 | 112 ± 9 |
| Blood gases | | | |
| PH | 7.44 ± 0.02 | 7.44 ± 0.02 | 7.44 ± 0.02 |
| PO2, mmHg | 118 ± 3 | 109 ± 4 | 112 ± 6 |
| PCO2, mmHg | 39.2 ± 0.6 | 39.6 ± 0.5 | 41.0 ± 1.3 |
| During MCAo (15 min) | | | |
| Body Temperature, ° C. | 36.9 ± 0.09 | 36.7 ± 0.15 | 36.8 ± 0.23 |
| MABP, mmHg | 116 ± 9 | 111 ± 6 | 98 ± 6 |
| After MCAo (15 min) | | | |
| Body Temperature, ° C. | 36.9 ± 0.09 | 36.8 ± 0.08 | 36.8 ± 0.12 |
| After MCAo (24 hr) | | | |
| Body Temperature, ° C. | 36.6 ± 0.14 | 37.0 ± 0.25 | 36.5 ± 0.14 |
| Body weight, g | 238 ± 6 | 244 ± 6 | 250 ± 5 |

MABP: Mean arterial blood pressure
*P < 0.05, Student's t-test

TABLE 2

Physiological Variables in Post-Treatment MCAO Study

| Physiological Variables | Control (n = 10) | TAT-NR2BAA (n = 8) | TAT-NR2B9c (n = 9) |
| --- | --- | --- | --- |
| Before anesthesia | | | |
| Body weight, g | 314 ± 4 | 301 ± 5 | 306 ± 7 |
| Before MCAo (15 min) | | | |
| Body Temperature, ° C. | 36.9 ± 0.07 | 36.7 ± 0.07 | 36.6 ± 0.07 |
| MABP, mmHg | 103 ± 4 | 103 ± 6 | 103 ± 5 |
| Blood gases | | | |
| PH | 7.43 ± 0.01 | 7.45 ± 0.01 | 7.43 ± 0.02 |
| PO2, mmHg | 113 ± 4 | 113 ± 4 | 105 ± 4 |
| PCO2, mmHg | 39.4 ± 1.0 | 37.9 ± 1.1 | 40.1 ± 1.0 |
| During MCAo (15 min) | | | |
| Body Temperature, ° C. | 36.9 ± 0.07 | 36.7 ± 0.11 | 37.0 ± 0.07 |
| MABP, mmHg | 120 ± 5 | 121 ± 5 | 119 ± 8 |
| Blood gases | | | |
| PH | 7.44 ± 0.01 | 7.46 ± 0.01 | 7.43 ± 0.01 |
| PO2, mmHg | 113 ± 3 | 108 ± 2 | 111 ± 4 |
| PCO2, mmHg | 39.3 ± 0.7 | 48.0 ± 1.2 | 39.8 ± 0.9 |

TABLE 2-continued

Physiological Variables in Post-Treatment MCAO Study

| Physiological Variables | Control (n = 10) | TAT-NR2BAA (n = 8) | TAT-NR2B9c (n = 9) |
|---|---|---|---|
| During MCAo (60 min) | | | |
| Body Temperature, °C. | 37.1 ± 0.21 | 37.0 ± 0.31 | 36.7 ± 0.11 |
| MABP, mmHg | 146 ± 5 | 149 ± 4 | 143 ± 5 |
| During MCAo (65 min) | | | |
| Body Temperature, °C. | 37.1 ± 0.16 | 37.0 ± 0.29 | 36.9 ± 0.08 |
| MABP, mmHg | 134 ± 6 | 136 ± 5 | 137 ± 4 |
| After MCAo (15 min) | | | |
| Body Temperature, °C. | 37.0 ± 0.09 | 36.9 ± 0.23 | 36.8 ± 0.08 |
| MABP, mmHg | 128 ± 6 | 116 ± 4 | 119 ± 4 |
| After MCAo (24 hr) | | | |
| Body Temperature, °C. | 36.6 ± 0.14 | 36.7 ± 0.27 | 36.4 ± 0.24 |
| Body weight, g | 276 ± 3 | 276 ± 6 | 279 ± 8 |

MCAo: Middle cerebral artery occlusion; MABP: Mean arterial blood pressure

Although this disclosure has described and illustrated certain preferred embodiments of the invention, it is to be understood that the invention is not restricted to those particular embodiments. Rather, the invention includes all embodiments which are functional or mechanical equivalence of the specific embodiments and features that have been described and illustrated.

I claim:

1. A method of reducing the damaging effect of excitotoxicity in a mammal having the excitotoxicity, said method comprising the step of administering an effective amount of an agent comprising a tSXV-containing peptide comprising the sequence KLSSIESDV [SEQ ID NO:1] and an internalization peptide to the mammal to reduce the damaging effect.

2. The method as defined in claim 1, wherein said tSXV-containing peptide is administered with a pharmaceutical carrier as a pharmaceutical composition.

3. The method of claim 1, wherein the excitotoxicity is due to traumatic injury.

4. The method of claim 1, wherein the excitotoxicity is due to ischemia.

5. The method of claim 4, wherein said ischemia is selected from the group consisting of cerebral ischemia, global cerebral ischemia and cerebral stroke.

6. The method of claim 4, wherein said ischemia results from a decrease in central nervous system tissue perfusion with blood.

7. The method of claim 6 wherein said decrease in central nervous system tissue perfusion is associated with a pathological condition selected from the group consisting of vessel thrombosis, vasospasm, luminal occlusion by an embolic mass.

8. A method for protecting against the damaging effect of excitotoxity to the brain or spinal cord in a mammal, said method comprising administering to the mammal an effective amount of an agent comprising a tSXV-containing peptide comprising the sequence KLSSIESDV [SEQ ID NO:1] and an internalization peptide to protect against the damaging effect of excitotoxicity.

9. The method as defined in claim 8, wherein said tSXV-containing peptide is administered with a pharmaceutical carrier as a pharmaceutical composition.

10. The method of claim 8, wherein the excitotoxicity is due to ischemia.

11. The method of claim 8, wherein the excitotoxicity is due to traumatic injury.

12. A method of reducing the damaging effect of stroke in a patient having stroke, comprising administering to the patient an effective amount of an agent comprising a tSXV-containing peptide comprising the sequence KLSSIESDV [SEQ ID NO:1] and an internalization peptide to reduce the damaging effect of the stroke.

13. The method as defined in claim 12, wherein said tSXV-containing peptide is administered with a pharmaceutical carrier as a pharmaceutical composition.

14. The method of claim 12, wherein the agent is administered as a single bolus injection after the onset of cerebral ischemia.

15. The method of claim 14, wherein the agent is administered one hour after onset of cerebral ischemia.

* * * * *

UNITED STATES PATENT AND TRADEMARK OFFICE
CERTIFICATE OF CORRECTION

PATENT NO. : 7,595,297 B2  
APPLICATION NO. : 10/208374  
DATED : September 29, 2009  
INVENTOR(S) : Michael Tymianski Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 843 days.

Signed and Sealed this

Twenty-eighth Day of September, 2010

David J. Kappos
*Director of the United States Patent and Trademark Office*

SEQUENCE LISTING

```
<160> NUMBER OF SEQ ID NOS: 6

<210> SEQ ID NO 1
<211> LENGTH: 9
<212> TYPE: PRT
<213> ORGANISM: Homo sapiens

<400> SEQUENCE: 1

Lys Leu Ser Ser Ile Glu Ser Asp Val
1               5

<210> SEQ ID NO 2
<211> LENGTH: 11
<212> TYPE: PRT
<213> ORGANISM: Human immunodeficiency virus

<400> SEQUENCE: 2

Tyr Gly Arg Lys Lys Arg Arg Gln Arg Arg Arg
1               5                   10

<210> SEQ ID NO 3
<211> LENGTH: 12
<212> TYPE: PRT
<213> ORGANISM: Homo sapiens

<400> SEQUENCE: 3

Cys Ser Lys Asp Thr Met Glu Lys Ser Glu Ser Leu
1               5                   10

<210> SEQ ID NO 4
<211> LENGTH: 11
<212> TYPE: PRT
<213> ORGANISM: Human immunodeficiency virus

<400> SEQUENCE: 4

Lys Ala Leu Gly Ile Ser Tyr Gly Arg Lys Lys
1               5                   10

<210> SEQ ID NO 5
<211> LENGTH: 9
<212> TYPE: PRT
<213> ORGANISM: Homo sapiens
```

```
<400> SEQUENCE: 5

Lys Leu Ser Ser Ile Glu Ala Asp Ala
1               5

<210> SEQ ID NO 6
<211> LENGTH: 9
<212> TYPE: PRT
<213> ORGANISM: Homo sapiens

<400> SEQUENCE: 6

Lys Leu Ser Ser Ile Glu Thr Asp Val
1               5
```